US010119960B2

(12) United States Patent
Chae et al.

(10) Patent No.: US 10,119,960 B2
(45) Date of Patent: Nov. 6, 2018

(54) METHOD OF SCREENING CANCER CELLS USING WRINKLE PATTERNS ON A THIN MEMBRANE

(71) Applicant: ARIZONA BOARD OF REGENTS ON BEHALF OF ARIZONA STATE UNIVERSITY, Scottsdale, AZ (US)

(72) Inventors: Junseok Chae, Scottsdale, AZ (US); Jennie Appel, Tempe, AZ (US); Joseph Liao, Stanford, CA (US)

(73) Assignees: Arizona Board of Regents on Behalf of Arizona State University, Scottsdale, AZ (US); The Board of Trustees of the Leland Stanford Junior University, Stanford, CA (US); The U.S. Government represented by the Department of Veteran Affairs, Washington, DC (US)

( * ) Notice: Subject to any disclaimer, the term of this patent is extended or adjusted under 35 U.S.C. 154(b) by 0 days.

(21) Appl. No.: 15/316,710

(22) PCT Filed: Jun. 9, 2015

(86) PCT No.: PCT/US2015/034929
§ 371 (c)(1),
(2) Date: Dec. 6, 2016

(87) PCT Pub. No.: WO2015/191600
PCT Pub. Date: Dec. 17, 2015

(65) Prior Publication Data
US 2017/0191989 A1 Jul. 6, 2017

Related U.S. Application Data

(60) Provisional application No. 62/009,677, filed on Jun. 9, 2014.

(51) Int. Cl.
*G01N 33/50* (2006.01)
*G01N 21/84* (2006.01)
*G01N 33/487* (2006.01)
*G01N 33/574* (2006.01)

(52) U.S. Cl.
CPC ..... *G01N 33/5091* (2013.01); *G01N 21/8422* (2013.01); *G01N 33/487* (2013.01); *G01N 33/574* (2013.01)

(58) Field of Classification Search
None
See application file for complete search history.

(56) References Cited

PUBLICATIONS

Appel, Jennie; et al; "Wrinkle Cellomics: Screening Bladder Cancer Cells Using an Ultra-Thin Silicone Membrane" Micro Electro Mechanical Systems, IEEE 27th International Conference, Jan. 26-30, 2014, 889-892 (Year: 2014).*

(Continued)

*Primary Examiner* — David W Berke-Schlessel
(74) *Attorney, Agent, or Firm* — Quarles & Brady LLP

(57) ABSTRACT

Systems and methods for performing cancer screening assays are disclosed. The disclosed systems and methods use a thin film comprising cross-linked polysiloxane. At least a portion of a biological sample to be assayed is contacted with the thin film, along with a cell culture media. After a subsequent incubation period, the thin film is visualized to detect a wrinkle pattern (or lack thereof). The presence of one or more wrinkles and/or a higher degree of wrinkling in the thin film indicates the presence of cancer cells in the biological sample. The disclosed systems and methods can be incorporated into improved assays and kits for cancer screening.

32 Claims, 15 Drawing Sheets

(56) References Cited

PUBLICATIONS

Aldousari, et al., Update on the Management of Non-Muscle Invasive Bladder Cancer, Can. Urol. Assoc. J., 2010, 4(1):56-64.
Babjuk, Transurethral Resection of Non-Muscle-Invasive Bladder Cancer, European Urology Supplements, 2009, 8:542-548.
Beningo, et al., Flexible Substrata for the Detection of Cellular Traction Forces, Trends in Cell Biology, 2002, 12(2):79-84.
Cerda, et al., Geometry and Physics of Wrinkling, Physical Review Letters, 2003, 90(7):074302-1 thru 074302-4.
Cheung, et al., Recent Advances in the Diagnosis and Treatment of Bladder Cancer, BMC Medicine, 2013, 11:13, 8 pages.
Harris, et al., Silicone Rubber Substrata: A New Wrinkle in the Study of Cell Locomotion, Science, 1980, 208:177-179.
Huang, et al., Capillary Wrinkling of Floating Thin Polymer Films, Science, 2007, 317:650-653.
Ilyas, et al., Electrophysiological Analysis of Biopsy Samples Using Elasticity as an Inherent Cell Marker for Cancer Detection, Analytical Methods, 2014, 6:7166-7174.
Kim, et al., Actin Cap Associated Focal Adhesions and Their Distinct Role in Cellular Mechanosensing, Scientific Reports, 2012, 2:555, 13 pages.
Koch, et al., 3D Traction Forces in Cancer Cell Invasion, PLoS ONE, 2012, 7(3):e33476, 8 pages.
Kraning-Rush, et al., Cellular Traction Stresses Increase with Increasing Metastatic Potential, PLoS ONE, 2012, 7(2):e32572, 10 pages.
Lekka, et al., Elasticity of Normal and Cancerous Human Bladder Cells Studied by Scanning Force Microscopy, Eur. Biophys. J., 1999, 28:312-316.
Li, et al., Quantifying the Traction Force of a Single Cell by Aligned Silicon Nanowire Array, Nano Letters, 2009, 9(10)3575-3580.
Pelham, Jr., et al., High Resolution Detection of Mechanical Forces Exerted by Locomoting Fibroblasts on the Substrate, Molecular Biology of the Cell, 1999, 10:935-945.
Remmerbach, et al., Oral Cancer Diagnosis by Mechanical Phenotyping, Cancer Research, 2009, 69(5):1728-1732.
Tan, et al., Cells Lying on a Bed of Microneedles: An Approach to Isolate Mechanical Force, PNAS, 2003, 100(4):1484-1489.
Tomasini, et al., Urinary Markers/Cytology: What and When Should a Urologist Use, Urologic Clinics of North America, 2013, 40(2):165-173.
Wright, et al., Estimated Urine pH and Bladder Cancer Risk in a Cohort of Male Smokers (Finland), Cancer Causes and Control, 2005, 16(9):1117-1123.
PCT International Search Report and Written Opinion, PCT/US2015/034929, dated Sep. 1, 2015.

\* cited by examiner

METHOD OF SCREENING CANCER CELLS USING WRINKLE PATTERNS ON A THIN MEMBRANE

CROSS-REFERENCE TO RELATED APPLICATIONS

This application represents the national stage entry of PCT International Application No. PCT/US2015/034929 filed on Jun. 9, 2015 and claims the benefit of and priority from U.S. Provisional Patent Application Ser. No. 62/009,677 filed Jun. 9, 2014, which are incorporated by reference herein in their entirety for all purposes.

STATEMENT REGARDING FEDERALLY SPONSORED RESEARCH

This invention was made with government support under DGE1311230 awarded by the National Science Foundation. The government has certain rights in the invention.

BACKGROUND

The present disclosure relates generally to systems and methods for cancer screening and, in particular, to systems and methods for using the wrinkle patterns on thin membranes to determine whether cancer cells are present in a biological sample.

A variety of methods are used clinically to diagnose cancer in a patient. As a non-limiting example, in the United States, bladder cancer is the fifth most common cancer, with an estimated 72,570 new cases in 2013 [1]. Current diagnostic strategies include cystoscopy, the visual inspection of bladder lumen with an endoscope, and urine cytology, the microscopic inspection of cellular morphology derived from urine samples [1]. Cystoscopy is invasive and may not be able to differentiate between malignant and benign tumors [1]. Urine cytology, while non-invasive, has poor sensitivity and requires complex sample preparation and an experienced cytopathologist to interpret the results. Other non-invasive techniques include detection of cancer biomarkers in urine samples. Such methods are not always reliable, in that they depend on the number of cancerous cells present in the urine sample [2].

Therefore, given the above, there is a need for improved and simplified methods for screening for the presence of cancer in a patient.

SUMMARY

The disclosed systems and methods overcome the aforementioned drawbacks by providing simple, reliable, non-invasive methods for screening for the presence of cancer cells in a biological sample. In contrast to urine cytology, the disclosed system requires minimal sample preparation and does not require significant expertise to interpret the results. The disclosed system is comprised of an ultra-thin silicone membrane and exploits the distinct biophysical properties of various cell types and cancerous variants. The silicone membrane is deformed by cellular forces applied by cancerous cells and not by the non-cancerous controls. Thus a wrinkle pattern is generated selectively by cancerous cells.

No prior work has applied wrinkle patterns to screen for cancerous cells from complex bodily fluids, such as blood or urine. Our work here is the foundation for the development of a small-size and non-invasive device that avoids the complexity of sophisticated instrumentation to identify presence of cancerous cells in a clinical sample. The rapid screening of urine samples, as well as various other sample types, will improve the early detection of cancer, permit less invasive therapies and enhance human health.

Accordingly, in a first aspect, the disclosure encompasses a method for detecting the presence of one or more cancer cells in a biological sample. The method includes the steps of (a) contacting a thin film comprising a cross-linked polysiloxane with at least a portion of a biological sample and a culture media; and (b) detecting the presence or absence of one or more wrinkles in the thin film. The presence of one or more wrinkles in the thin film indicates that the biological sample contains one or more cancer cells. Optionally, the polysiloxane may be cross-linked by heating a composition comprising polysiloxane (a silicone).

In some embodiments, the cross-linked polysiloxane is a cross-linked polydimethylsiloxane. In an exemplary embodiment, the cross-linked polydimethylsiloxane is a cross-linked liquid silicone.

In some embodiments, the thin film is between 5 nm and 1,000 nm thick. In some such embodiments, the thin film is between 5 nm and 500 nm thick, between 5 nm and 100 nm thick, or between 10 nm and 50 nm thick.

In some embodiments, the step of detecting the presence or absence of one or more wrinkles in the thin film is performed by visually inspecting the thin film. Optionally, visually inspecting the thin film may be performed using conventional light microscopy.

In some embodiments, the cancer cells are bladder cancer cells.

In some embodiments, the biological sample comprises a fluid selected from urine, blood, saliva, lymph, or cerebrospinal fluid.

In a second aspect, the disclosure encompasses a method of screening for cancer in a subject. The method includes the steps of (a) contacting a thin film comprising a cross-linked polysiloxane with a culture media and at least a portion of a biological sample obtained from the subject; and (b) detecting the wrinkle pattern of the thin film. The nature of the wrinkle pattern indicates the potential presence of cancer in the subject. Optionally, the polysiloxane may be cross-linked by heating a composition comprising polysiloxane (a silicone).

In some embodiments, the wrinkle pattern is detected by visualizing the thin film. Optionally, the thin film may be visualized using conventional light microscopy.

In some embodiments, the wrinkle pattern is quantitatively measured. In some such embodiments, a higher quantity of wrinkles in the wrinkle pattern indicates a higher likelihood of the subject having cancer. Alternatively, a greater length for the wrinkles in the wrinkle patter indicates a higher likelihood of the subject having cancer.

In some embodiments, the cross-linked polysiloxane is a cross-linked polydimethylsiloxane. In one embodiment, the cross-linked polydimethylsiloxane is cross-linked liquid silicone.

In some embodiments, the thin film is between 5 nm and 1,000 nm thick. In some such embodiments, the thin film is between 5 nm and 500 nm thick, between 5 nm and 100 nm thick, or between 10 nm and 50 nm thick.

In some embodiments, the type of cancer that is screened for is bladder cancer.

In some embodiments, the biological sample comprises a fluid selected from urine, blood, saliva, lymph, or cerebrospinal fluid.

In a third aspect, the disclosure encompasses a kit for performing a cancer screening assay. The kit includes (a) a thin film having a thickness of from 5 nm to 500 nm comprising a cross-linked polysiloxane; and (b) a media for culturing cells.

In some embodiments, the cross-linked polysiloxane is a cross-linked polydimethylsiloxane. In one such embodiment, the cross-linked polydimethylsiloxane is a cross-linked liquid silicone.

In some embodiments, the thin film is between 5 nm and 100 nm thick, or between 10 nm and 50 nm thick.

The foregoing and other advantages of the invention will appear from the following description.

DETAILED DESCRIPTION

Figure 1:
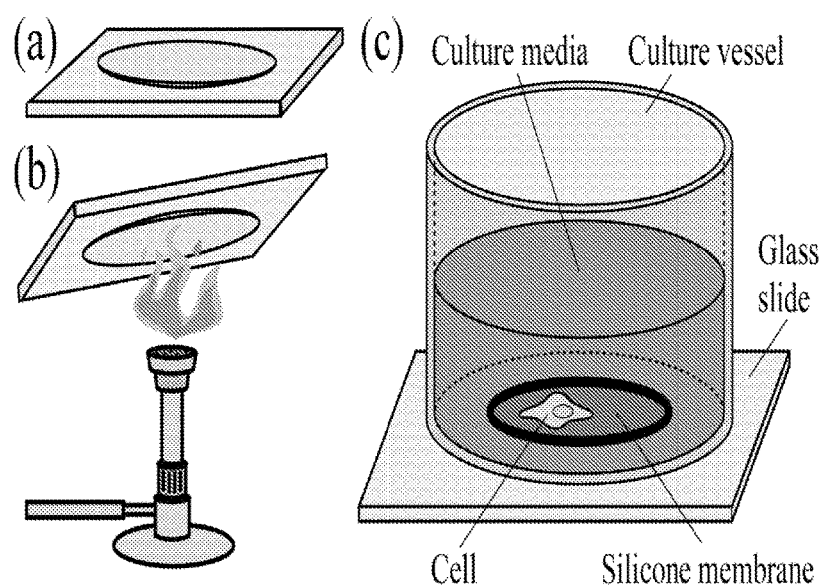
FIGS. 1(a)-1(c) are schematic illustrations of one embodiment of the disclosed method. 1(a) Fill the 1.5 cm diameter, 0.5 mm depth well with 12,500 cps liquid silicone. 1(b) Flash heat the liquid silicone, effectively cross-linking the polymer to form an ultra-thin membrane. 1(c) Using vacuum grease to adhere cell culture chambers to glass slide and fill the chamber with culture media and cells.

This invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference for all purposes.

Different cell types and cancerous variants have been shown to have distinct biophysical properties. Numerous methods have been explored to quantify the biophysical properties of cells, permitting the analysis of biological systems as mechanical systems. For example, Lekka et al. measured the Young's modulus—a measure of the stiffness of a material—of a variety of cell types with scanning force microscopy. The Young's modulus of a bladder cancer cells were determined to be approximately an order of magnitude smaller compared to normal [3].

Cancer cells have a tendency to spread out more, have a high degree of focal adhesions in contact with a surface and exert a stronger force on the surface than normal cells. Traction and adhesion forces are commonly studied to determine the force a cell exerts when it is interacting with a surface. In 2003, Tan et al. reported a micro-pillar MEMS structure to study these forces. The apex of the micro-pillars would bend due to the applied cellular adhesion forces, and through pillar characterization the adhesion force could be determined [4]. This unique micro-pillar method, however, requires sophisticated fabrication techniques.

As an alternate approach, the wrinkling of a thin membrane has been applied recently to exploit the difference of the Young's modulus of a cell. Huang et al. developed an ultra-thin polystyrene membrane and induced a sinusoidal wrinkle pattern on the membrane using water droplets [5]. Harris et al. reported previously a silicone membrane that visualized the traction forces generated during cellular locomotion. They approximated these forces using a flexible weighted probe [6]. Further refinement of this approach has included embedding fluorescent beads within the membrane to aid in tracking cell locomotion [7]. Despite the considerable effort expended for measuring the Young's modulus and cellular forces of different cell types, these approaches have yet to be implemented for the design of a diagnostic device to differentiate between cancerous and healthy cells.

The present disclosure describes a visualization platform, comprised of an ultra-thin silicone membrane, to differentiate between the biophysical properties of cancerous and non-cancerous cells from human patients. Cancerous cells adhere to, spread on, and induce deformation of this membrane to produce wrinkles, while non-cancerous cells fail to generate wrinkles. Wrinkle patterns—number, length, and direction of wrinkles—can be visualized by conventional microscopy. Quantitative measurement of these wrinkling patterns represents a powerful, non-invasive diagnostic tool for prevalent cancers, such as bladder cancer.

The thin films used as cell culture substrates in the disclosed systems and methods comprise a cross-linked polysiloxane. Also known as "silicones," polysiloxanes are mixed inorganic-organic polymers with the chemical formula $[R_2SiO]_n$, where R is an organic group such as methyl, ethyl, or phenyl. These materials consist of an inorganic silicon-oxygen backbone ( . . . —Si—O—Si—O—Si—O— . . . ) with organic side groups attached to the silicon atoms, which are four-coordinate. Common polysiloxanes that can be cross-linked to form the thin film cross-linked silicone membrane used in the disclosed systems and methods include without limitation linear polydimethylsiloxane (PDMS) and various silicone resins formed by branched and/or cage-like oligosiloxanes.

When cross-linked, polysiloxanes can form a rubber-like material that is commonly referred to as "silicone rubber." Cross-linking can be accomplished using a number of methods known in the art, including without limitation free radical catalysts, strong acids, or heat. In certain exemplary embodiments, an ultrathin film of silicone rubber is produced by quick exposure of the surface of a liquid silicone composition with an intense source of heat, such as the flame of a Bunsen burner.

Silicone rubber is inert and non-toxic, making it useful for medical applications. Silicone rubber membranes are known in the art to support monolayer cell adhesion in culture, and thin silicone rubber films are transparent, thus facilitating visualizing the cells cultured on such films.

In the disclosed methods, at least part of a biological sample and a cell culture media is contacted with the thin cross-linked silicone film, and the system is incubated for a period of time. Subsequently, wrinkles or wrinkle patterns (or an absence thereof) are detected within the thin cross-linked silicone film. Wrinkle patterns may include without limitation the number, length, and directions of wrinkles appearing in the thin film. Based on the specific wrinkle patterns exhibited or the number of wrinkles detected, the method can be used to determine the presence or absence of cancer cells in the biological sample, thus forming the basis for a cancer screening assay.

The following examples are offered for illustrative purposes only, and are not intended to limit the scope of the present invention in any way. Indeed, various modifications of the invention in addition to those shown and described herein will become apparent to those skilled in the art from the foregoing description and the following example and fall within the scope of the appended claims.

Example 1

Wrinkle Cellomics

Screening Bladder Cancer Cells Using an Ultra-Thin Silicone Membrane

In this Example, we demonstrate the use of the disclosed method to differentiate between biological samples containing cancer cells and biological samples that do not contain cancer cells. The cells in the biological samples are incubated and cultured on a thin silicone membrane. Cancer cells induce a characteristic wrinkle pattern in the underlying membrane. In the absence of cancer cells, no such wrinkle pattern is induced in the membrane. These results demonstrate the feasibility of using the disclosed method for diagnosing cancer in a patient.

Visualization Platform.

Fabrication.

Fabrication of the ultra-thin silicone membrane begins with filling a 15 mm diameter by 0.5 mm deep well in a glass slide with high viscosity (12,500 cP) liquid silicone, as shown in FIG. 1(a). Then we invert the slide over a low flame (Bunsen burner) effectively cross-linking the polymer chains in the liquid silicone forming a thin crust or membrane, FIG. 1(b). After sanitizing (20% ethanol) the culture chamber we apply a layer of vacuum grease to it and press it onto the glass slide creating a water tight seal in the area surrounding the membrane, FIG. 1(c).

Characterization.

The physical properties of our ultra-thin silicone membrane were characterized with the addition of minute water droplets to its surface; the water droplets deformed the membrane producing a discrete wrinkle pattern [5]. The thickness of the membrane was determined to be approximately 28 nm from the observed number of wrinkles caused by deformation of the membrane. To obtain predictive estimation of the wavelength, amplitude and number of wrinkles, we consider the 1D out-of-plane displacement of an initially flat sheet of area (=W×L, W is width and L is length) as a function of spatial dimension (=ξ(x,y)) (FIG. 2(a)). The thickness of the sheet, t, is much smaller than W and L, where 0<y<W also, for simplicity, W<<L.

When a stretching strain ε is applied in the x direction, then the total energy of the system is:

$$U = U_B + U_S - L \quad (1)$$

Here $U_B$ is the bending energy due to deformation in the y direction:

$$U_B = \tfrac{1}{2} \int B (\partial_y^2 \zeta)^2 dA \quad (2)$$

where B is the bending stiffness. $U_S$ is the stretching energy in presence of tension T(x):

$$U_S = \tfrac{1}{2} \int T(x)(d_x \zeta)^2 dA \quad (3)$$

Boundary conditions:

$$\int_0^L \left[ \tfrac{1}{2} (\partial_y^2 \zeta)^2 - \frac{\Delta(x)}{w} \right] dy = 0 \quad \zeta(0, y) = 0 \quad \zeta(L, y) = 0$$

Figure 2:
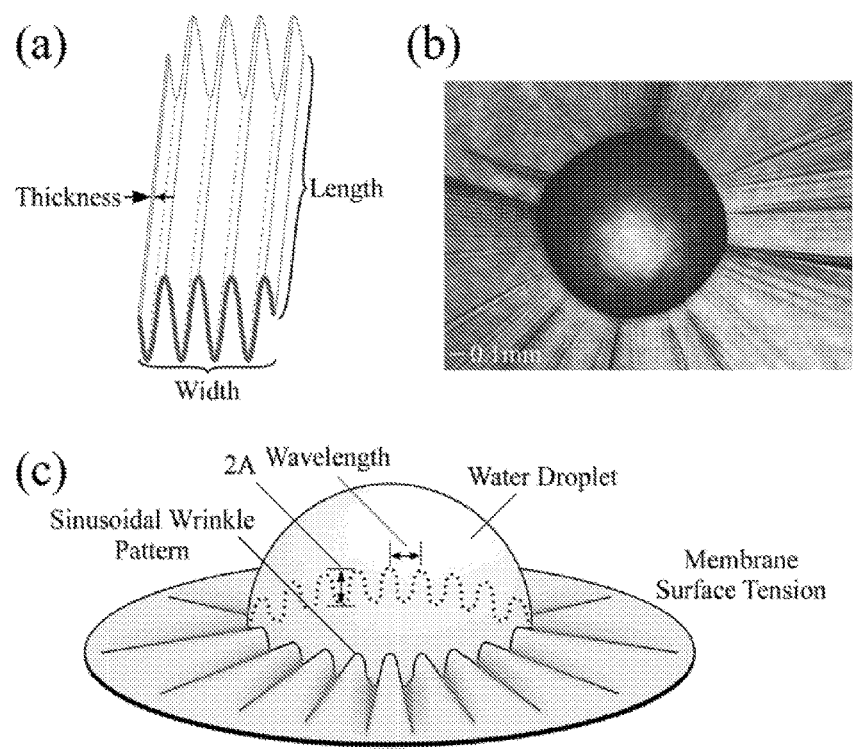
FIG. 2(a) is a schematic of wrinkles in a flat soft sheet induced by a force in the x direction.
FIG. 2(b) is a schematic demonstrating the sinusoidal wrinkle pattern, due to capillary forces acting upon an ultra-thin membrane.
FIG. 2(c) shows a ~0.2 mg, 1.1 mm diameter water droplet acting on ultra-thin membrane causing the formation of 148 wrinkles (approximately >0.4 mm long).
Figure 3:
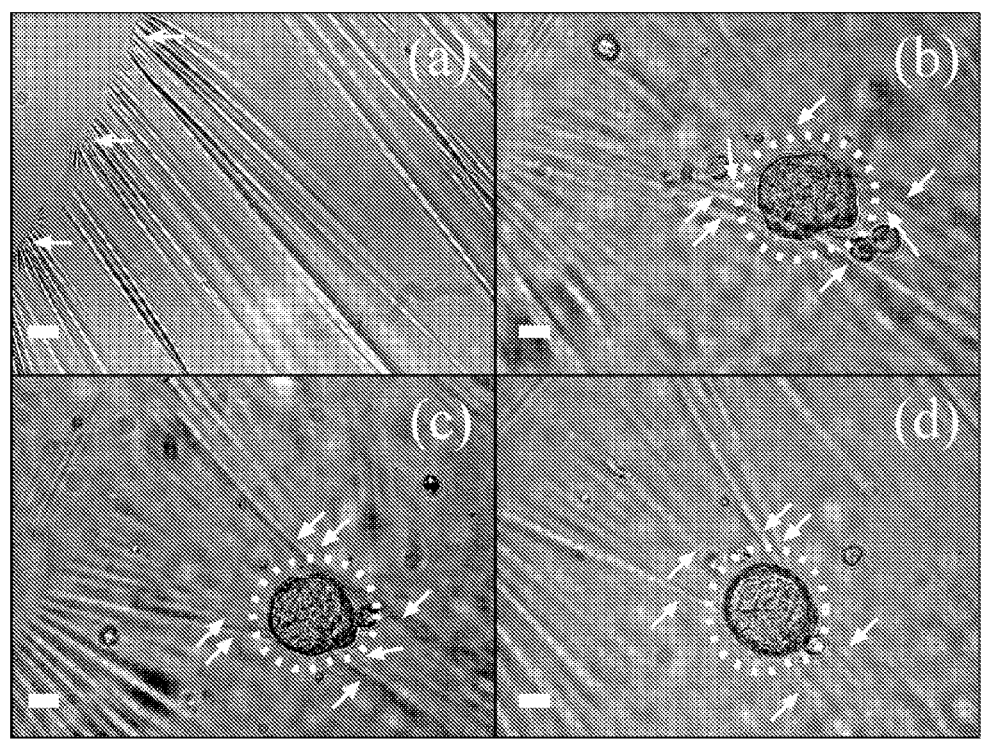
FIGS. 3(a)-(d) are photographs taken of a representative membrane after adding media and after incubation with cancer cells. 3(a) shows representative membrane after adding 1 mL of media. Membrane fabrication and adding media sometimes induces pre-existing wrinkles (white arrows). Cancerous (RT4) cells after 3(b) 18-hr, 3(c) 20-hr, and 3(d) 22-hr incubation in a 37° C. 5% $CO_2$. RT4 cell cluster distorts pre-existing wrinkles, deforming their natural shape (dotted enclosure indicates the cluster). Scale bar is 20 µm.

After applying boundary conditions we determine:

$$\lambda = \frac{\sqrt{2\pi L t}}{\sqrt[4]{3(1-v)^2 \varepsilon}} \quad (4)$$

$$A = \left(\sqrt{vLt}\right)\left(\sqrt[4]{\frac{16\varepsilon}{3\pi^2(1-v^2)}}\right) \quad (5)$$

where λ is the wavelength and A is the amplitude of the sinusoidal wrinkling shown in FIG. 2(c), L is the length of the membrane, t is the thickness of the membrane, v is the Poisson's ratio of the membrane, and ε is the strain of the membrane. We approximated the number of wrinkles by dividing the wavelength of the wrinkle pattern by the circumference of the water droplet (πd/λ), where d is the diameter of the droplet.

TABLE 1

Derived equations for λ, A and number of wrinkles for patterns generated by capillary action of a 1.1 mm diameter water droplet (~0.2 mg). The calculated number of wrinkles with approximated v and ε had an error of 24% compared with the measured value.

| Property | Calculated | Measured |
|---|---|---|
| Wavelength | 30.7 μm | ~23.3 μm |
| Amplitude | 7.1 μm | N/A |
| # of Wrinkles | 113 | 148 |
| Thickness | N/A | ~28 nm |

The wavelength, amplitude and number of wrinkles were calculated with an assumed thickness of 50 nm, a Poisson's ratio of 0.48 and a strain of 0.299. With a membrane length of 2.5 mm and a water droplet diameter of 1.1 mm, we calculated the wavelength, amplitude and number of wrinkles (Table 1). The measured wavelength, amplitude and number of wrinkles for a ~0.2 mg water droplet was determined by applying the water to our membrane and observing wrinkle formations under Nomarkski imaging (FIG. 2(b)). Our calculated 113 wrinkles had a 24% error when compared to the measured 148 wrinkles.

Materials and Methods.

Cell Culture.

RT4 transitional bladder cancer cells were grown in McCoy's 5A modified media (Life Technologies Corp. 16600-082) supplemented with 10% fetal bovine serum (FBS Life Technologies Corp. 10082-139) and 1× penicillin/streptomycin (Sigma-Aldrich Co. P4333-20ML). Human embryonic kidney cells, HEK293f, were grown in eagle's minimum essential medium (ATCC 30-2003) supplemented with 10% FBS and 1× penicillin/streptomycin incubated at 37° C. in humidity and 5% $CO_2$.

Sample Preparation.

Cells at 70% confluency were trypsinized for 5 min at 37° C., inactivated with 10% FBS, pelted by centrifugation at 300× gravity for 5 min, resuspended in culture media and $5 \times 10^5$ cells were applied to each device. For buffy coat device testing, $5 \times 10^5$ cells of buffy coat (Innovative Research) was first applied to the ultra-thin membrane prior to applying cancerous (RT4) or non-cancerous (HEK293f) cells.

Results and Discussion.

Following the characterization of our ultra-thin silicone membrane, we explored our device for discerning cancerous cells. We performed a time-lapse experiment for 0-hr, 18-hr, 20-hr, and 22-hr, to determine the onset and persistence of membrane wrinkling induced by RT4 cells (FIG. 3(a)-(d))

Initially, at 18 hours incubation (b) we have 7 wrinkles with an average length of 180 µm, two hours later at 20 hours incubation (c) the same 7 wrinkles remain with an average length of 170 µm, and finally after an additional two hours at 22 hours incubation (d) 6 wrinkles remain with an average length of 170 µm, showing that the number and length of wrinkles produced by RT4 cells after 18 hours were consistent and did not change over the time interval.

We separately incubated $5 \times 10^5$ bladder cancer cells RT4 and human embryonic kidney epithelial HEK293f cells on our membranes. One hour following adhesion to the membrane, RT4 cells induced wrinkle formation with two distinct wrinkles formed under these cancerous cells (FIG. 4(a)), while 14 hours following adhesion to the membrane, HEK293f cells failed to induce any wrinkles (FIG. 4(b)). Cancerous cells exerted significantly stronger adhesion forces on the membrane when compared to non-cancerous cells.

Clinical urine samples often contain a high concentration of white blood cells when infection or other diseases such as cancer are present. These white blood cells have the potential to obscure or influence membrane wrinkle formation by cancerous cells. To more accurately replicate these patient sample conditions, we explored testing in the context of commercially available buffy coat, a combination of white blood cells and platelets purified from human blood. After 6 hours of incubation buffy coat cells fell out of suspension and appeared to have adhered to the membrane. After an additional 14 hours these cells failed to induce any wrinkles (FIG. 4(c)).

To determine if a heterogeneous cell population would affect cancerous cell wrinkle formation on the ultra-thin membrane. We tested cancerous RT4 cells in combination with non-cancerous HEK293f and buffy coat cells. HEK293f cells are an epithelial cell line, thus they approximate the cells found in human urine samples. The presence of HEK293f and white blood cells did not influence the membrane wrinkle formation, FIG. 4(d).

Figure 5:
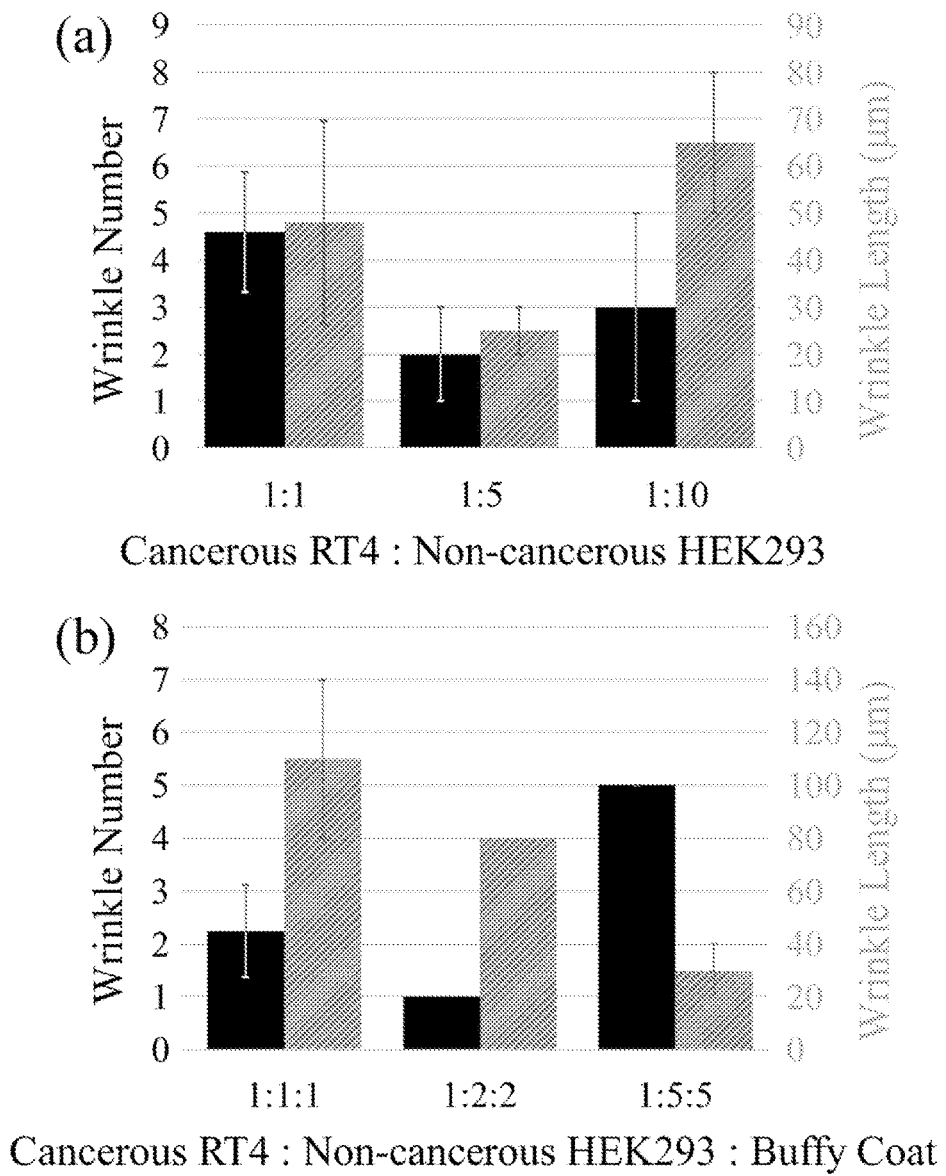
FIG. 5(a) is a bar graph characterizing wrinkles (number of wrinkles: solid bars, wrinkle length: dashed bars) induced by cancerous RT4 cells. Mixed samples of RT4 and HEK293f cells at ratios of 1:1, 1:5, and 1:10, respectively were incubated on ultra-thin silicone membrane for 16 hours at 37° C. 5% $CO_2$.
FIG. 5(b) is a bar graph characterizing wrinkles induced by cancerous RT4 cells. Mixed samples of RT4, HEK293f and buffy coat cells at ratios of 1:1:1, 1:2:2, and 1:5:5, respectively were incubated on ultra-thin silicone membrane for 20 hours at 37° C. 5% $CO_2$. Wrinkle lengths were measured by approximation based on a 20 µm fixed scale bar.

We next tested the ability of cancerous cells to induce membrane wrinkles in the presence of a high population of non-cancerous cells. After 16 hours incubation the cancer cells in each mix ratios produced a similar number and length of membrane wrinkles (FIG. 5(a)). This suggests the wrinkle characteristics on the membrane are rather independent of mixture ratio.

We further tested the ability of cancerous cells to induce membrane wrinkles in the simultaneous presence of a high population of non-cancerous and white blood cells. Furthermore, these mixed samples of 1:1:1, 1:2:2, and 1:5:5, RT4 to HEK293f to buffy coat, are more realistic to patient urine samples. After 20 hours of incubation, the cancer cells in each of the mix ratios produced a similar number and length of membrane wrinkles (FIG. 5(b)).

Conclusion.

This Example demonstrates that an ultra-thin silicone membrane can serve as a visualization platform to differentiate between cancerous and non-cancerous cells based on membrane wrinkle patterns. Our system exploits the fundamental difference in cell biophysical properties, ensuring the accuracy and sensitivity for cancer detection. The disclosed method facilitates rapid cancer detection, early diagnosis and improved human health.

REFERENCES CITED (BACKGROUND, DETAILED DESCRIPTION AND EXAMPLE 1)

[1] American Cancer Society. Cancer.org. 2013.
[2] G. Cheung, A. Sahai, M. Billia, P. Dasgupta, and M. S. Khan, "Recent advances in the diagnosis and treatment of bladder cancer," *BMC medicine*, vol. 11, p. 13, 2013.
[3] M. Lekka, P. Laidler, D. Gil, J. Lekki, Z. Stachura, and a. Z. Hrynkiewicz, "Elasticity of normal and cancerous human bladder cells studied by scanning force microscopy," *European biophysics journal: EBJ*, vol. 28, pp. 312-6, 1999.
[4] J. L. Tan, J. Tien, D. M. Pirone, D. S. Gray, K. Bhadriraju, and C. S. Chen, "Cells lying on a bed of microneedles: an approach to isolate mechanical force," *Proceedings of the National Academy of Sciences of the United States of America*, vol. 100, pp. 1484-9, 2003.
[5] J. Huang, M. Juszkiewicz, W. H. de Jeu, E. Cerda, T. Emrick, N. Menon, et al., "Capillary wrinkling of floating thin polymer films," *Science* (New York, N.Y.), vol. 317, pp. 650-3, 2007.
[6] A. Harris, P. Wild, and D. Stopak, "Silicone Rubber Substrata: A New Wrinkle in the Study of Cell Locomotion Author(s): Albert K. Harris, Patricia Wild and David Stopak Reviewed work(s): Source: Science, New Series, Vol. 208, No. 4440 (Apr. 11, 1980), pp. 177-179 Publish," *Science* (New York, N.Y.), vol. 208, pp. 177-179, 1980.
[7] R. J. Pelham and Y. L. Wang, "High resolution detection of mechanical forces exerted by locomoting fibroblasts on the substrate," *Molecular biology of the cell*, vol. 10, pp. 935-45, 1999.

Example 2

Rapid Bladder Cancer Cell Detection from Clinical Urine Samples Using an Ultra-Thin Silicone Membrane In this Example, we demonstrate the disclosed method using clinical samples from patients.

Summary.

Early detection of initial onset, as well as recurrence, of cancer is paramount for improved patient prognosis and human health. Cancer screening is enhanced by rapid differentiation of cancerous from non-cancerous cells which employs the inherent differences in biophysical properties. This Example demonstrates that cell-line derived cancer cells deform our <30 nm silicone membrane within an hour and induce visually distinct wrinkle patterns, while cell-line derived non-cancerous cells fail to induce these wrinkle patterns. Accordingly, the disclosed method can be used for the rapid detection of cancerous cells from human clinical urine samples.

Specifically, we performed a double-blind study with cells extracted from the urine of human patients presenting cancer-like symptoms alongside samples containing healthy control cells. Wrinkle patterns were induced within 12 hours by the five cancer patient samples and not by the samples containing the healthy controls. These results were independently validated by standard diagnostic cystoscopy and cytology techniques. Thus, our ultra-thin membrane approach for cancer diagnosis appears to be as accurate as standard diagnostic methods, while being performed more rapidly, less invasively, and requiring limited expertise to perform.

Introduction.

Bladder cancer is the fifth most common cancer in the United States, with an estimated 74,000 new cases diagnosed in 2015 [1]. Since bladder cancer has a high rate of new tumor formation and a recurrence rate of up to 70%, lifelong surveillance as often as every 3 months is necessary. Such lifelong surveillance incurs significant expense and time commitment [2].

Current bladder cancer diagnosis is based on an invasive endoscopy procedure called cystoscopy, followed by biopsy of suspect lesions for histological examination. To compensate for cystoscopy, which lacks sensitivity for low grade flat carcinoma [2], urine cytology—the microscopic examination of naturally exfoliated and expelled urothelial cells in the urine—is widely employed alongside cystoscopy. While highly specific (>95%), urine cytology has low (~20%) and moderate (~60%) sensitivity for low and high grade cancers, respectively [3]. As a consequence of this low sensitivity for early cancer detection, there are strong interests to develop urine-based diagnostics to complement and overcome shortcomings of cytology and cystoscopy. The majority of such efforts have focused on developing molecular diagnostics based on cancer-associated genetic changes, as well as alterations in RNA and protein expression [4]. While several molecular assays are commercially available, significant shortcomings remain, which include diagnostic sensitivity and excessive cost, precluding widespread adaptation [4].

Quantitative measurement of cellular biophysical properties of cancerous and non-cancerous cells represents a promising alternative strategy for cancer diagnosis, given the intrinsic difference in cytoskeleton flexibility, morphology and stiffness of cancerous from non-cancerous cells. Young's modulus, a measurement of cellular stiffness, is particularly promising for cancerous cell detection [5-6]. For bladder cancer, Lekka et al. determined that cancerous cell lines HU456, T24, and BC3726 had an average Young's modulus of 0.8 kPa, compared with 10.0 kPa for non-cancerous cell lines HU609 and HCU29 [5]. For oral cancer, cells extracted from patients with oral squamous cell carcinoma were three-fold more flexible than non-cancerous cells from healthy donors [6]. Tan et al. also compared the translocation time, related to cytoskeleton flexibility, of T24, cell-line derived human bladder cancer cells, and immortalized non-cancerous human urothelial cells. These cell types were passed through a micro pore via an applied electric field. The non-cancerous urothelial cells had an order of magnitude increase in translocation time when compared to their cancerous counterparts [7]. Thus scanning force microscopy, optical stretching and translocation via applied electric field have all shown significant differences in the biophysical properties of cancerous and non-cancerous cells.

The differences in Young's modulus and cytoskeleton flexibility between cancerous and non-cancerous cells are in part due to another biophysical property, the cellular traction forces applied to an in vitro surface. Cell traction forces can be visualized using micro-pillar structures [8] or silicone membranes [9-10]. Li et al. employed a silicon nano-pillar structure to determine that cancerous human Hela cells exerted 20% greater cell traction force when compared to non-cancerous fibroblasts harvested from neonatal rat liver [11]. The application of micro-pillars as a diagnostic device requires highly-optimized fabrication techniques and sophisticated analytical methodologies. Although these methods all show distinct differences between the biophysical properties of cancerous and non-cancerous cells, they have not been employed for cancer cell detection.

In this Example, we report a high-throughput strategy capable of differentiating bladder cancer cells from non-cancerous cells based on their respective cellular traction forces. Our method requires minimal sample preparation, does not demand highly-trained personnel for data interpretation, and only involves a simple microscope. As previously reported, our approach leverages an ultra-thin, <30 nm, silicone membrane to visualize the distinct cell traction forces of bladder cancer cells. Our ultra-thin silicone membrane is deformed exclusively by cancerous cells, producing distinct wrinkle patterns compared to non-cancerous cells [12]. In this Example, we examined the underlying mechanism for ultra-thin membrane deformation exclusively by cancerous bladder cells by manipulation and visualization of focal adhesion proteins. Furthermore, clinical validation of our cancer detection strategy was performed. A double-blind study was performed using urine collected from five individuals presenting cancer-like symptoms. Within 12 hours of sample collection, cancer cells present in all five patient urine samples generated wrinkle patterns. Our technique circumvents traditionally complex, costly, and invasive instrumentation for bladder cancer screening and detection, and also may be applied for the detection of additional cancers.

Results and Discussion.

Ultra-Thin Membrane Characterization.

Silicone membranes have been employed previously to study the biophysical properties of cells, specifically cell traction forces [9-10]. To compare and confirm a similar membrane thicknesses from ours and other previous studies, we characterized the silicone membrane by applying a minute droplet of water to the surface [12,14]. The approximately 0.5 µL of water on the surface of membrane induced a radial wrinkle pattern (FIG. 6(b)). From the wrinkle pattern, the thickness of the membrane was calculated to be approximately 28 nm. A predictive estimation of the wavelength, amplitude and number of wrinkles is included in the Supplementary Text below [15].

Wrinkle Pattern from Cell-Line Derived Cancerous Cells.

Figure 7:
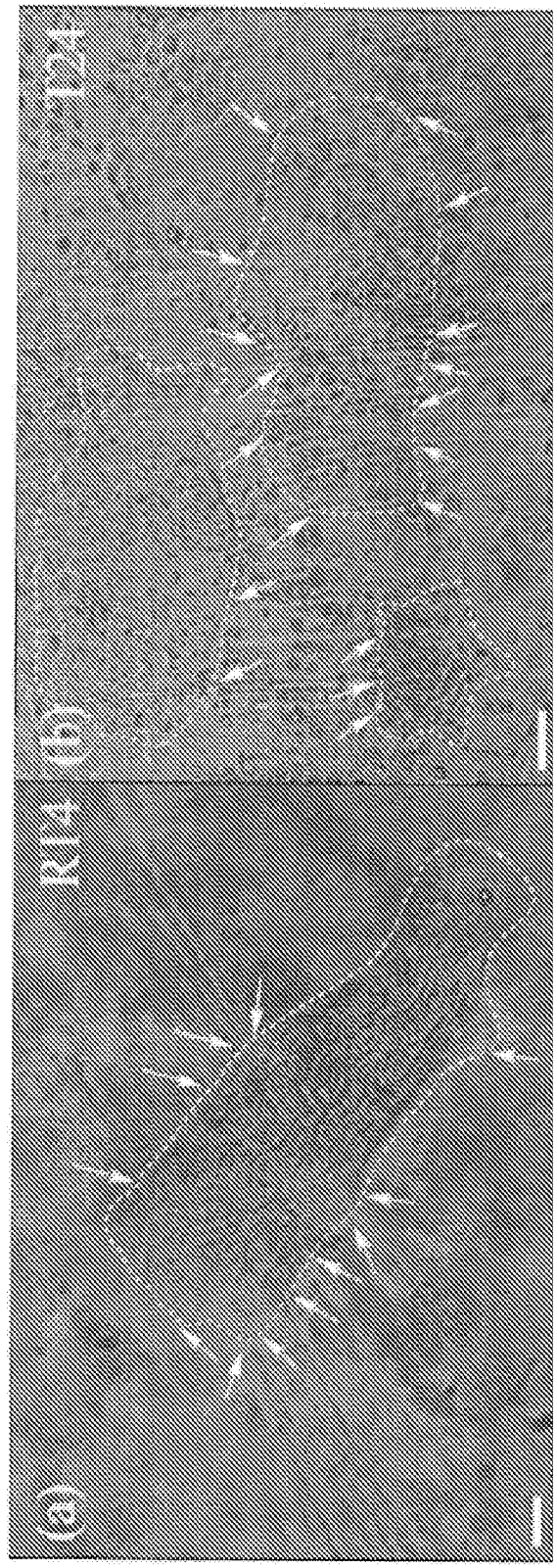
FIG. 7 shows wrinkle pattern formation and analysis. (a) Approximately 75 RT4 cells generating a wrinkle pattern which consists of 12 wrinkles with an average length of 75 µm, after more than 24 hours. (b) Approximately 150 T24 cells generating 3 wrinkle patterns, the top pattern consists of 5 wrinkles with an average length of 50 µm, the middle pattern consists of 13 wrinkles with an average length of 60 µm, and the bottom pattern consists of 3 wrinkles with an average length of 80 µm, after more than 24 hours. (c) Plot of the total number of wrinkle patterns generated by each cell type: RT4, T24, HEK293f, and Healthy Donor, at each time interval. (d) Plot showing the average attributes of a wrinkle pattern generated by either RT4 or T24 cells at each time interval. All scale bars are 20 µm.
Figure 7:
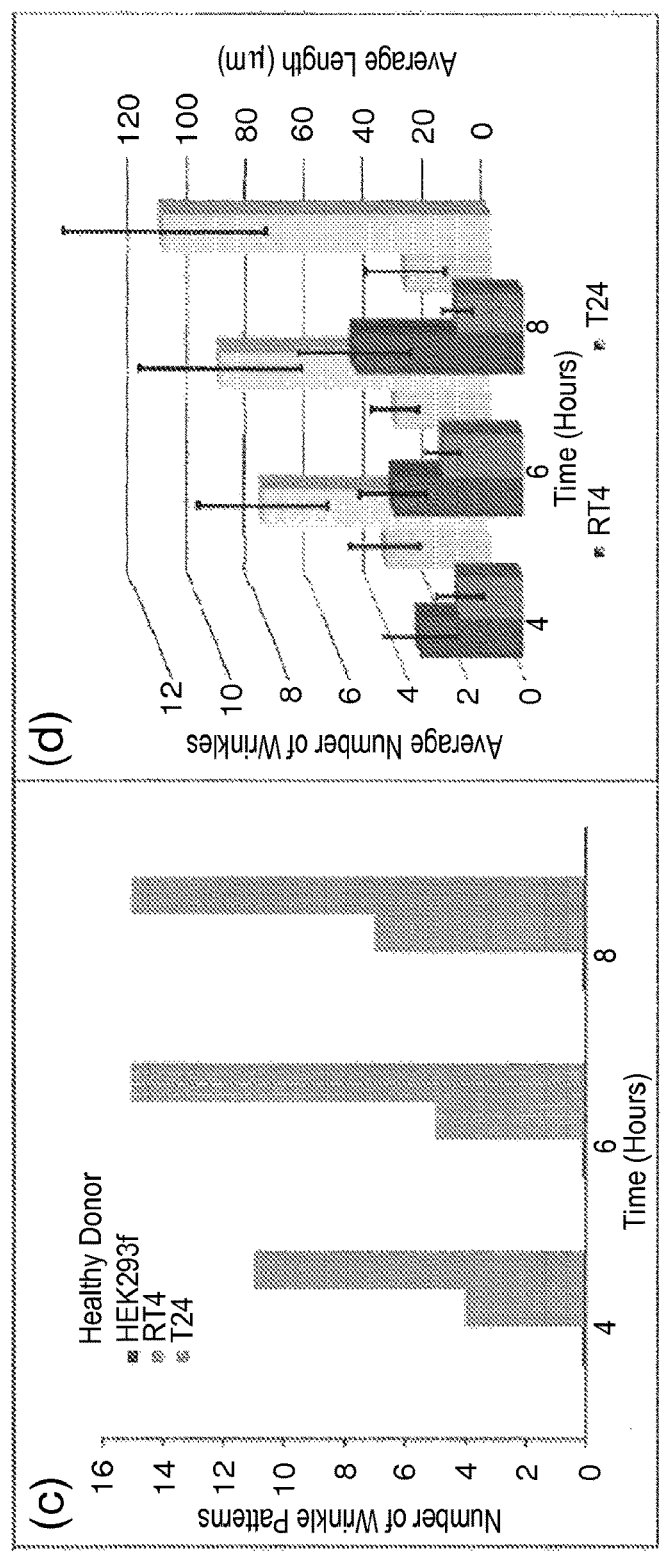
Figure 8:
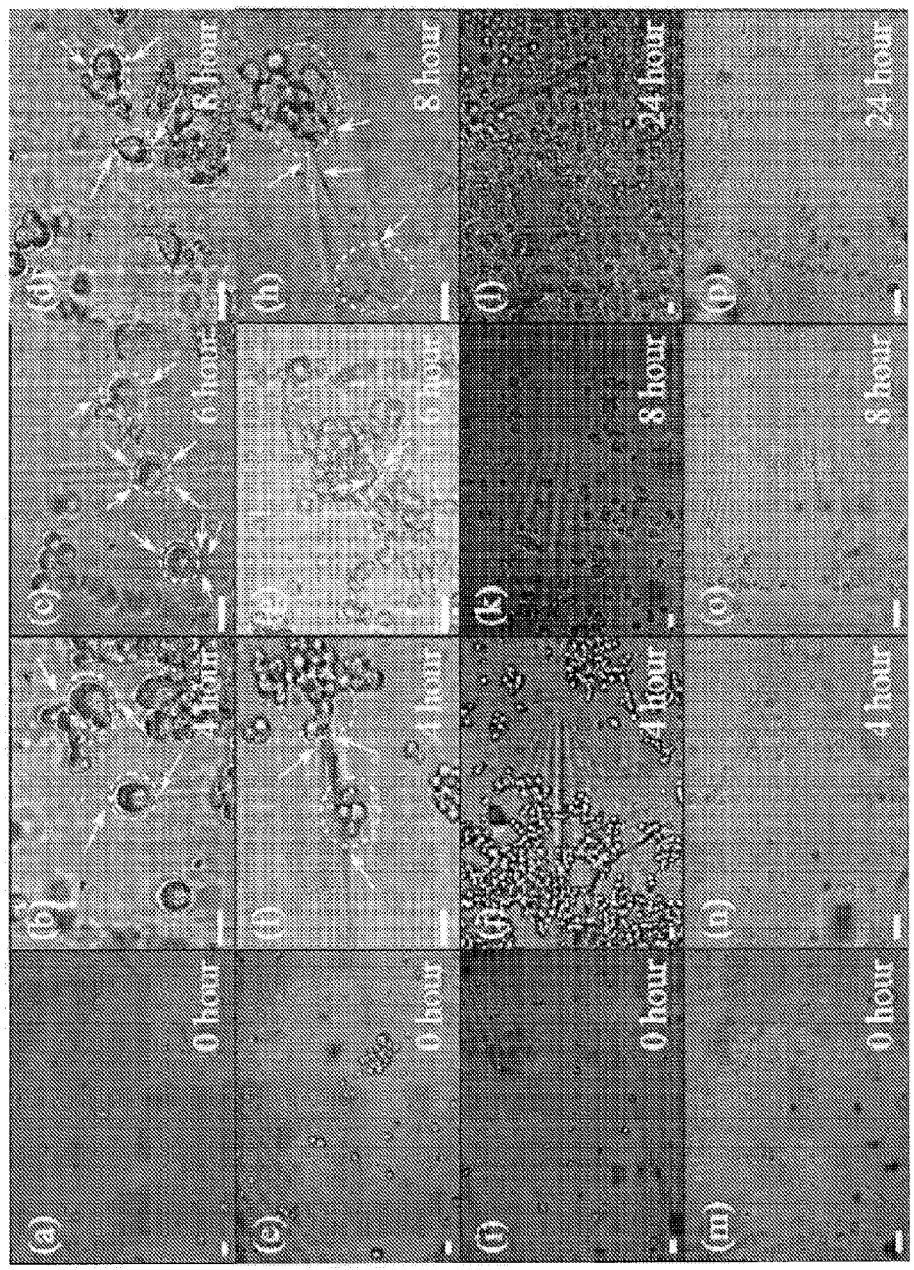
FIG. 8 shows time lapse of wrinkle pattern formation in all cell types. (a)-(d) RT4 cells at 0, 4, 6, & 8 hours, generating 3 wrinkle patterns after 4 hours, (e)-(h) T24 cells at 0, 4, 6, & 8 hours, generating 2 wrinkle patterns after 4 hours, (i)-(l) HEK293f cells at 0, 4, 8, & 24 hours, no wrinkle patterns are present, (m)-(p) healthy donor epithelial cells at 0, 4, 8, & 24 hours, no wrinkle patterns are present. All scale bars are 20 µm.

It has previously been demonstrated that the biophysical properties of a cell can be visually manifested by placement on a silicone membrane to induced wrinkle formation due to cell traction forces [9-10, 12]. We previously compared the time and extent of membrane wrinkle formation generated by cell-line derived low grade bladder papillary carcinoma RT4 cells, used as a control (FIG. 7(a)). In this Example, we evaluated and compared RT4 cells to a cell-line derived high grade bladder carcinoma T24 cells. Cancer grades represent tumor severity and the likelihood of metastasis within human patients. Approximately $5 \times 10^5$ RT4 or T24 cells were applied to our silicone membrane, and distinct wrinkles were generated by both within blank hours (FIGS. 7(a) and (b)).

To elucidate the onset of wrinkle pattern formation for cancerous RT4 and T24 cells, a time-lapse experiment was performed for 4-, 6-, and 8-hour incubation periods; as opposed to a previous time-lapse experiment using only RT4 cells at 18-, 20-, and 22-hour incubation periods [12]. Both the RT4 cells (FIGS. 8(a)-(d)) and the T24 cells (FIGS. 8(e)-(h)) induced wrinkle patterns after 4 hours of incubation. By examining the aggregate number of wrinkle patterns generated at various time intervals, we found a positive correlation between the number of wrinkles patterns and the time of incubation (FIG. 7(c)). In contrast, the number of individual wrinkles and the length of these wrinkles, which comprise individual wrinkle patterns, showed little direct correlation with the incubation time (FIG. 7(d)). For example, RT4 cells generated on average 5.7 individual wrinkles after 8 hours, while T24 cells generate 2.3 individual wrinkles. Our representative cancerous cells generated wrinkle patterns as early as four hours and the wrinkle patterns formed persisted over the entire length of observation.

To ensure that selectively cancerous cells induce wrinkle pattern formation on our ultra-thin silicone membrane, we used a non-cancerous healthy control of cell-line human kidney epithelial (HEK293f) cells. HEK293f cells were chosen due to the high degree of similarity between the epithelial cells found in the kidney and the bladder cavity. Approximately $5\times10^5$ HEK293f cells were applied to our membrane. Similar to our previously report, HEK293f cells failed to generate discernable wrinkle patterns or individual wrinkles (FIG. 8(i)-(l)) after extended incubation period of 24 hours [12]. Thus cell-induced wrinkle pattern formation was specific to the cancerous cell-line derived cells we tested and not shared with non-cancerous cell-line derived cells.

Figure 9:
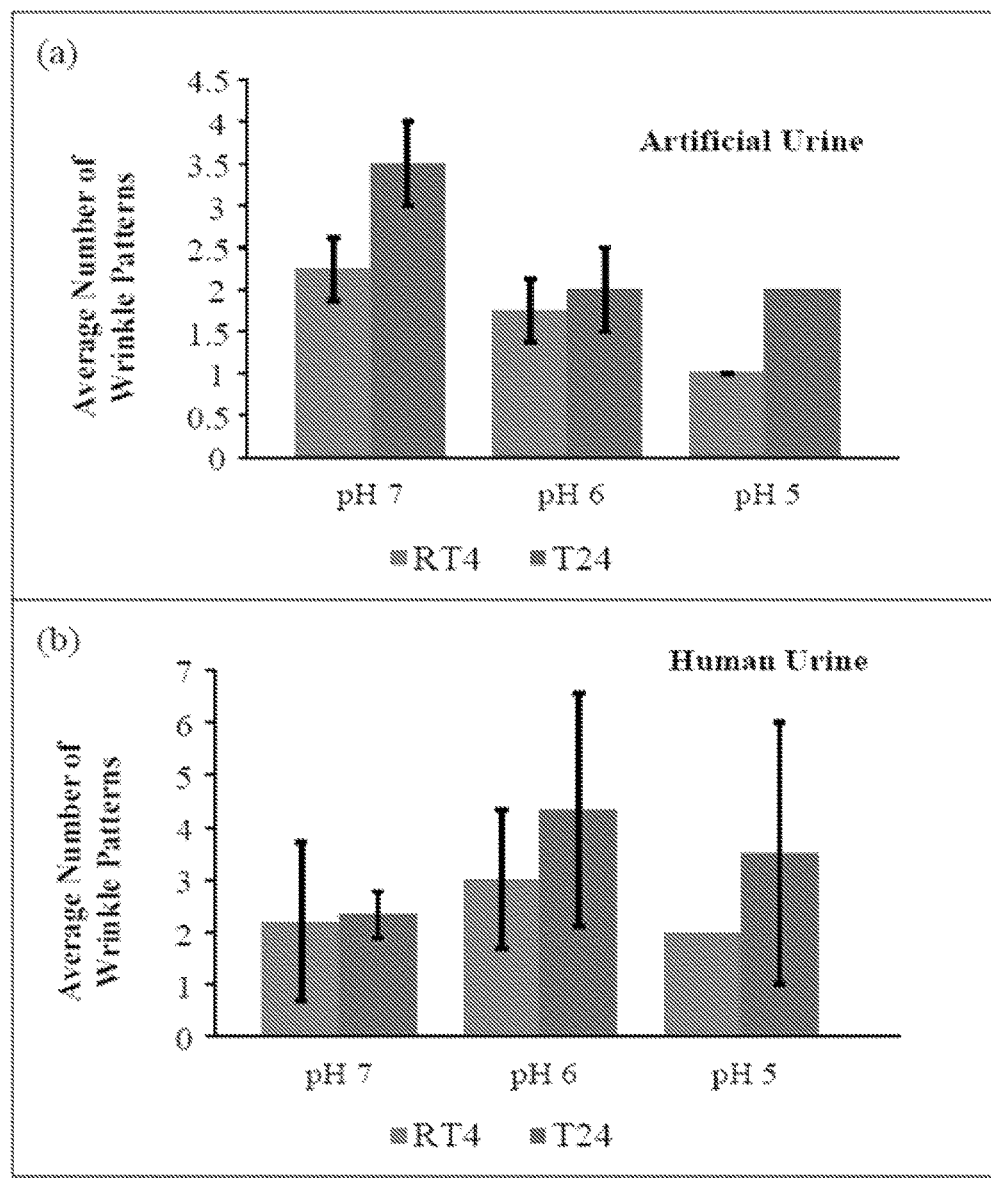
FIG. 9 shows analysis of wrinkle patterns in urine of varying pH Levels. (a) Plot of the average number of wrinkle patterns generated by either RT4 or T24 cells in artificial urine at various pH levels. (b) Plot of the average number of wrinkle patterns generated by either RT4 or T24 cells in a mix of purified healthy donor urine at various pH levels.

To better replicate potential clinical testing of human patient samples, we placed cell-line derived cancerous cells in modified urine environments. This simulates the conditions in which cells could not be readily extracted from human urine by centrifugation and instead whole urine samples would be applied to the membrane, such as in developing nations. We incubated cancerous RT4 or T24 cells on ultra-thin membranes in human (FIG. 9(b)) or artificial (FIG. 9(a)) urine at pH varying from 5 to 7, within the typical range of human urine [16]. To sustain the cancerous cell-line derived RT4 or T24 cells for extended device testing, we supplemented the clarified—by centrifugation—human or artificial urine with 10% fetal bovine serum. As expected, the cancerous RT4 and T24 cells retained the ability to induce membrane deformation and generated wrinkle patterns in both human and artificial urine, across all tested pH values. The average aggregate number of wrinkle patterns was not a function of the type of urine, human or artificial, or the pH value (FIG. 9). Thus the inherent biophysical properties differences responsible for cancer-specific wrinkle formation is not affected by the urine or changes in pH.

Wrinkle Patterns from a Mixture of Cancerous and Non-Cancerous Cells.

Figure 10:
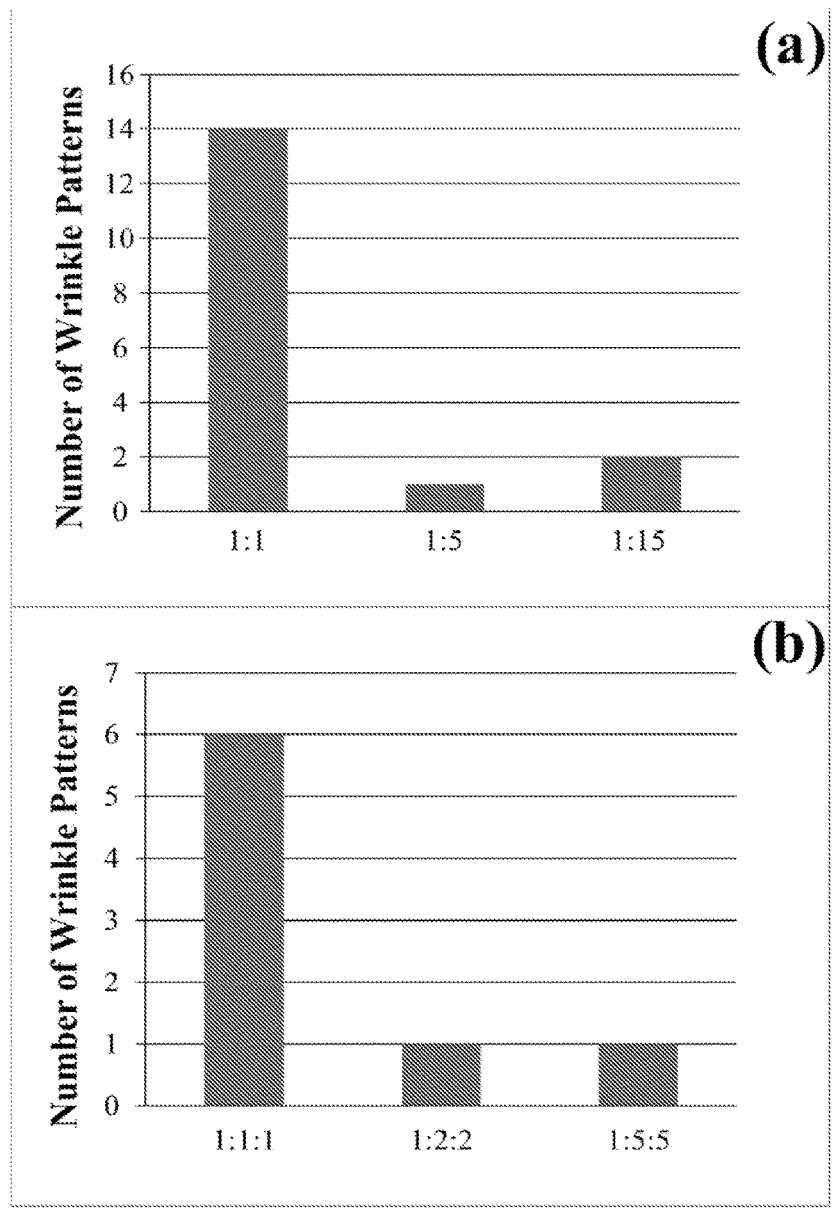
FIG. 10 shows wrinkle patterns in mixed cell populations. (a) Mix cell population, RT4 and HEK293f cells, approximately 10 RT4 cells generate 2 wrinkle patterns consisting of 2 and 3 wrinkles with an average length of 30 and 45 µm respectively, after 16 hours (data not shown). Plot shows the attributes of an average wrinkle pattern at each cell mix ratio (RT4:HEK293) after 16 hours. (b) Mix cell population, RT4, HEK293f, and buffy coat cells, approximately 10 RT4 cells generate a wrinkle pattern consisting of 2 wrinkles with an average length of 80 µm, after 20 hours (data not shown). Plot shows the attributes of an average wrinkle pattern at each cell mix ratio (RT4:HEK293:buffy coat), after 20 hours.

Our previous work examined the capacity of cancerous RT4 cells to generate wrinkle patterns in the presence of non-cancerous cells HEK293f and buffy coat cells [12]. Buffy coat is the fraction of blood that is comprised principally of white blood cells. White blood cells are often found in clinical patient urine, as one of the primary symptoms of bladder cancer is hematuria or blood within the urine. Our previous analysis examined the attributes of the present wrinkle patterns, i.e. number and length of wrinkles within each wrinkle pattern. Quantitation of the number of wrinkles within a wrinkle pattern was performed by serially counting the number of wrinkles generated by each cluster of cancerous cells or an individual cancerous cell. The length of each wrinkle within a wrinkle pattern was measured relative to the diameter of a cell, approximated as 20 µm. There was no apparent correlation between mixture ratio and these wrinkle pattern attributes. However, there was a strong inverse trend between the overall number of wrinkle patterns and mixture ratio (FIGS. 10(a) & (b)).

Wrinkle patterns are defined as the culmination of wrinkles generated by a cluster or individual cell within a discrete span separate from other cells and induced membrane deformations of the ultra-thin membrane. Therefore by examining the overall number of wrinkle patterns we can better represent clinical use of the ultra-thin membrane diagnosis platform, because a clinician would only need to determine if wrinkle patterns are present. Clinical patient urine samples are composed of a very small population of cancerous cells in the presence of an overwhelmingly non-cancerous cell population. Therefore increasing the number of non-cancerous cells better simulates clinical samples. Additional experimentation by varying mixture ratios to deplete the population of cancerous cells is necessary to define a true threshold for detection. However, in clinical applications approximations of the actual number of cancer cells present in a urine sample could be determined based on the number of wrinkle patterns present.

Clinical Urine Sample Testing.

To validate the ultra-thin membrane as a detection tool of human patient bladder cancer, we obtained urine samples from five individuals presenting cancer-like symptoms. All patients were male ages 53 to 89, and four of the five patients were being treated for a recurrence of bladder cancer. Additionally, two of the five patients reported a history of smoking.

Urine samples were collected during a trans-urethral resection of bladder tumor (TURBT) procedure, which is the current standard for bladder cancer diagnosis [13]. Also a control urine sample was collected via urination from a female healthy donor, age 26, with no family history of bladder cancer and only a single grandparent with lung cancer likely linked to smoking. Cells were extracted from all urine samples, washed and applied to the ultra-thin membrane.

Figure 11:
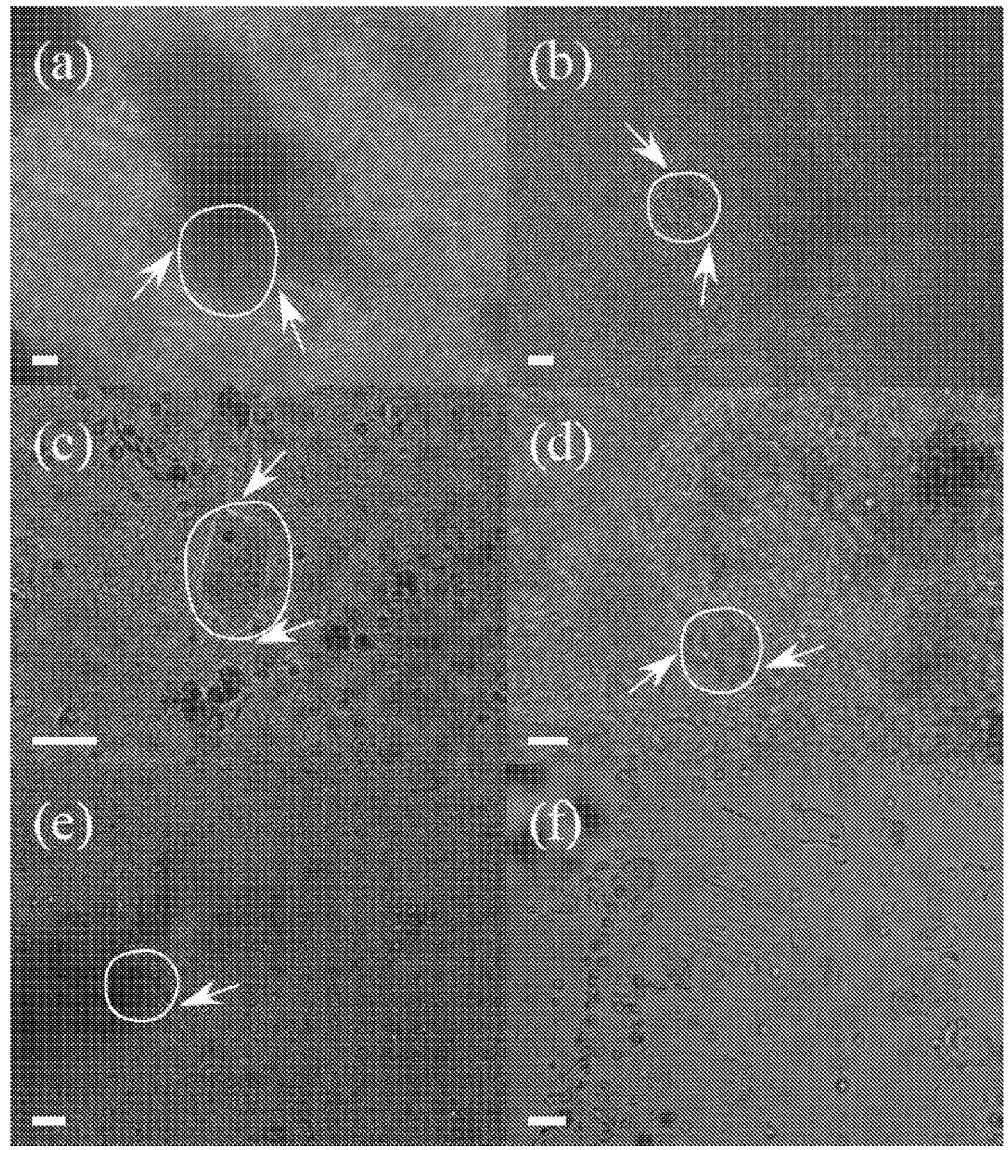
FIG. 11 shows wrinkle patterns formed by clinical patient samples. (a) wrinkle pattern generated by patient 1 after 24 hours; (b) wrinkle pattern generated by patient 2 after 24 hours; (c) wrinkle pattern generated by patient 5 after 12 hours; (d) wrinkle pattern generated by patient 3 after 24 hours; (e) wrinkle pattern generated by patient 4 after 12 hours; (f) no wrinkle patterns generated by healthy donor control. All scale bars are 20 µm.

Following 12 hours of incubation, wrinkle patterns were observed in the five bladder cancer patient samples (FIG. 11). Additionally, the healthy donor control cells failed to generate wrinkle patterns even after an extended incubation period of 24 hours (FIGS. 8(m)-(p)). The actual number of wrinkle patterns observed (Table 2), ranging from 1 to 5, corresponds to less than a wrinkle pattern per ultra-thin membrane. This indicates that despite the low concentration of cancer cells, practical use of the ultra-thin membrane for cancer detection is well within the membrane detection limit, which is dependent on the concentration of cancer cells in the urine sample.

Standard diagnosis method, TURBT, confirmed the five patients had bladder cancer. TURBT is performed by an endoscopic examination of the bladder interior and upon finding abnormal tissue extracting a small biopsy. This biopsy is then sent for examination by an experienced cytopathologist. As a complementary diagnosis method urine cytology is performed. This method is also dependent on an experienced cytopathologist to extract cells from urine and examine for abnormal cellular structure. For the purposes of this experiment, patients had previously undergone either cytology, cystoscopy or both before TURBT (Table 2). However, the patient prognosis was unknown until after analysis of the biopsy collected during TURBT. Interestingly, of the five patient samples, two—patient #2 and #3—demonstrated false negative results, i.e. negative for malignancy, by standard urine cytology, while generating an accurate positive result on our ultra-thin silicone membrane. Thus, initial validation of our ultra-thin silicone membrane demonstrates that this platform is highly sensitive and accurate for the detection of human patient bladder cancer from urine samples.

Validation of Cell Traction Forces that Generate Wrinkle Patterns.

Figure 12:
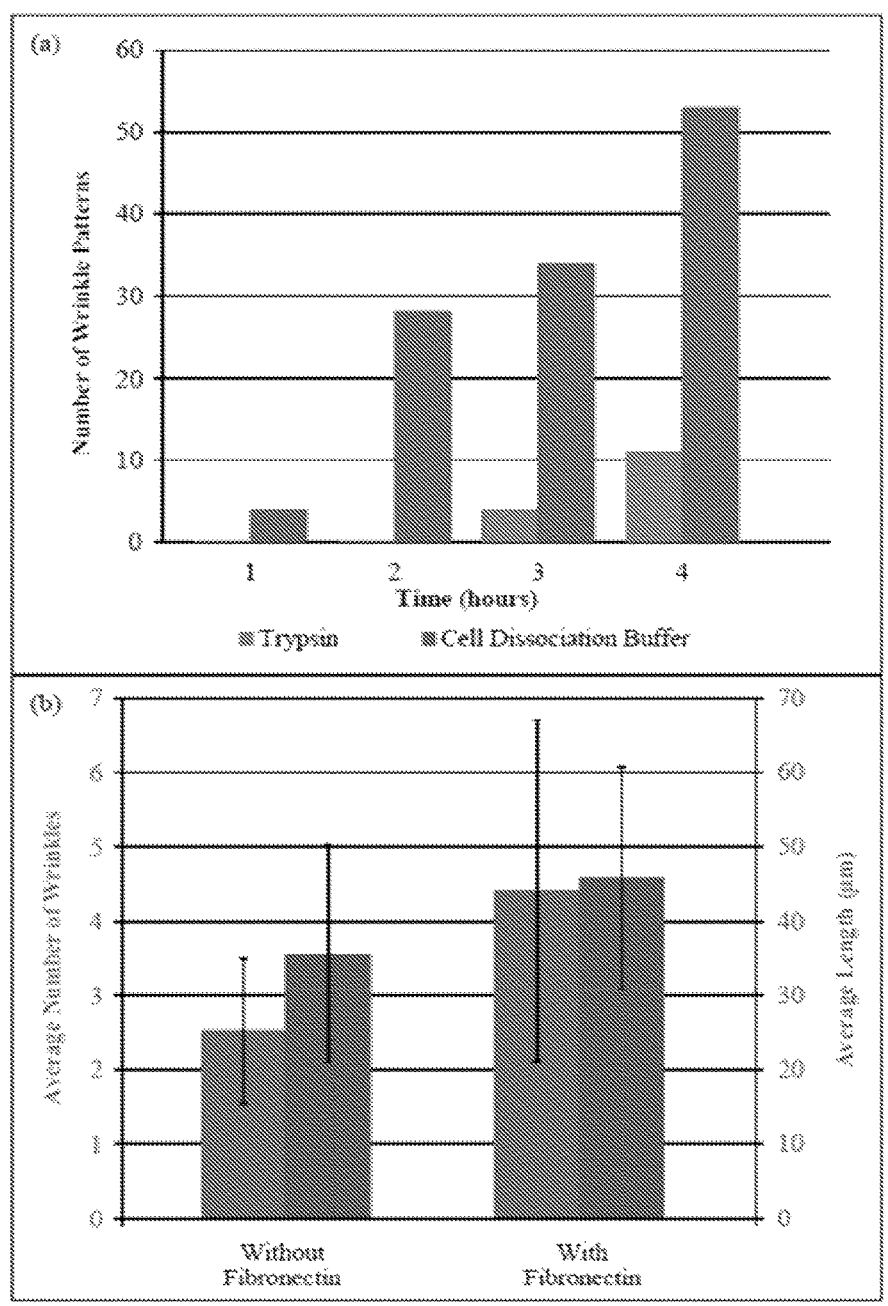
FIG. 12 compares cell transfer methods and adhesion promoting proteins. (a) Plot of the total number of wrinkle patterns generated over time after being transferred using either trypsin or a cell dissociation buffer. (b) Plot of the average attributes of a wrinkle pattern generated by RT4 cells after 12 hours in either unmodified devices or devices coated with fibronectin.

To further characterize and identify the working mechanism of wrinkle pattern formation, we varied the cell transfer method. T24 cells were removed from culture dishes by the addition of the protease trypsin or a cell dissociation buffer applied to our ultra-thin silicone membranes and imaged at 1 hour intervals for a total of four hours. While the T24 cells treated with the protease trypsin required three hours for initial wrinkle pattern formation, the T24 cells treated with the cell dissociation buffer generated wrinkles within a single hour (FIG. 12(a)). The initial transfer method relied on trypsin, which physically severs the focal adhesion proteins on the surface of the cell which must be regrown prior to cell-induced wrinkle formation. By shifting to a cell dissociation buffer, the focal adhesion proteins remain intact which dramatically reduces the time for wrinkle pattern formation, by negating regeneration of the adhesion protein. Therefore, we were able to decrease the time for cancerous cell wrinkle formation to one hour post cell addition to our membrane by changing the cell transfer method.

In an effort to make wrinkle patterns generated by RT4 cells more distinctive, we investigated a means of increasing the individual attributes of wrinkle patterns. We attempted to increase the individual number and length of wrinkles within a wrinkle pattern by coating the membrane with fibronectin, a cellular adhesion promoting protein. However, the average number and average length of wrinkles did not significantly vary with the addition of fibronectin (FIG. 12(b)). Treatment of our ultra-thin silicone membrane surface with fibronectin failed to significantly affect the induction of membrane wrinkles measured by the number or length of individual wrinkles within wrinkle patterns.

of our ultra-thin silicone membrane to produce wrinkle patterns. The observed strain induced deformation of our membrane by cancerous RT4 cells was compared to previously reported strain generated by cancerous cells [7]. Water droplet calibration of the membrane approximated 0.1% to 0.4% lumped strain (FIG. 6(b)). This correlates well with lump strain we derived from a study of cell traction forces of on a polydimethylsiloxane micro-pillar structure, which was estimated to be 0.5% lump strain [7]. We derived this lump strain by averaging the strain generated by the displacement of each micro-pillar. This averaged strain was then normalized by the ratio between the surface area of each pillar in contact with the cell over the total area of the cell [7]. Additionally, a positive correlation between cellular traction force and metastatic potential of cancerous cells has been reported [17-18]. Thus the strain, as measured by cell traction forces, visualized by the number of wrinkles within a wrinkle pattern, could be applied for discerning the grade of a cancer cell.

Cell traction forces are responsible for inducing strain in the ultra-thin membrane; these forces are dependent on focal adhesion proteins. Filamentous-actin (f-actin), a focal adhesion protein integral for cell shape, relocates to the edges of the cell for cell locomotion and spreading upon a surface [19]. Thus a focus of f-actin indicates that a force is being applied by the cell to an external surface [19].

To verify that the cytoskeleton of cancerous cells induces membrane deformation and generates wrinkle patterns in our ultra-thin silicone membrane, we fluorescently stained the f-actin with philotoxin. Philotoxin specifically binds to f-actin and the co-localization of philotoxin adjacent to wrinkle patterns would strongly support cellular adhesion being responsible for the membrane deformation. Following

TABLE 2

Comparison of Clinical Patient Diagnosis Methods and Wrinkle Pattern Detection. Relevant patient information, including sex, age, prior cystoscopy and cytology results, as well as the observation of wrinkle pattern formation and the aggregate number of wrinkle patterns for each patient sample is included, if applicable.

| Patient | Sex/Age | Urine Collection Method | Cystoscopy | Cytology | Diagnosis | Wrinkle Patterns | Number of Wrinkle Patterns |
|---|---|---|---|---|---|---|---|
| 1 | M/53 | TURBT | (Oct. 23, 2014) recurrence of bladder tumor at right UO, possibly involving distal right ureter | (Oct. 23, 2014) few atypical papilliary-like structures are seen associated with bland appearing urothelial cells. The findings are atypical. | non-invasive papillary carcinoma low grade | Yes | 2 |
| 2 | M/71 | TURBT | small papillary recurrence at bladder neck on recent surveillance cystoscopy | (Nov. 5, 2014) Negative for malignancy | non-invasive papillary carcinoma low grade | Yes | 2 |
| 3 | M/89 | TURBT | (Nov. 6, 2014) recurrent small bladder tumor near L UO | (Nov. 5, 2014) Negative for malignancy | non-invasive papillary urothelial carcinoma low grade | Yes | 1 |
| 4 | M/80 | TURBT | Not Available | (Nov. 6, 2014) atypical, there are cells with hyperchromatic nuclei, irregular nuclear contour and prominent nucleoli. Differential diagnosis includes reactive changes and neoplasia. | non-invasive papillary urothelial carcinoma high grade | Yes | 1 |
| 5 | M/67 | TURBT | Not Available | (Nov. 3, 2014) suscipicious for malignancy (urothelial cells with enlarged nuclei, high N:C ratios and irregular nuclear contours.) | non-invasive papillary carcinoma low grade | Yes | 5 |
| 6 | F/26 | Urination | Not Available | Not Available | Healthy Control | No | N/A |

Figure 13:
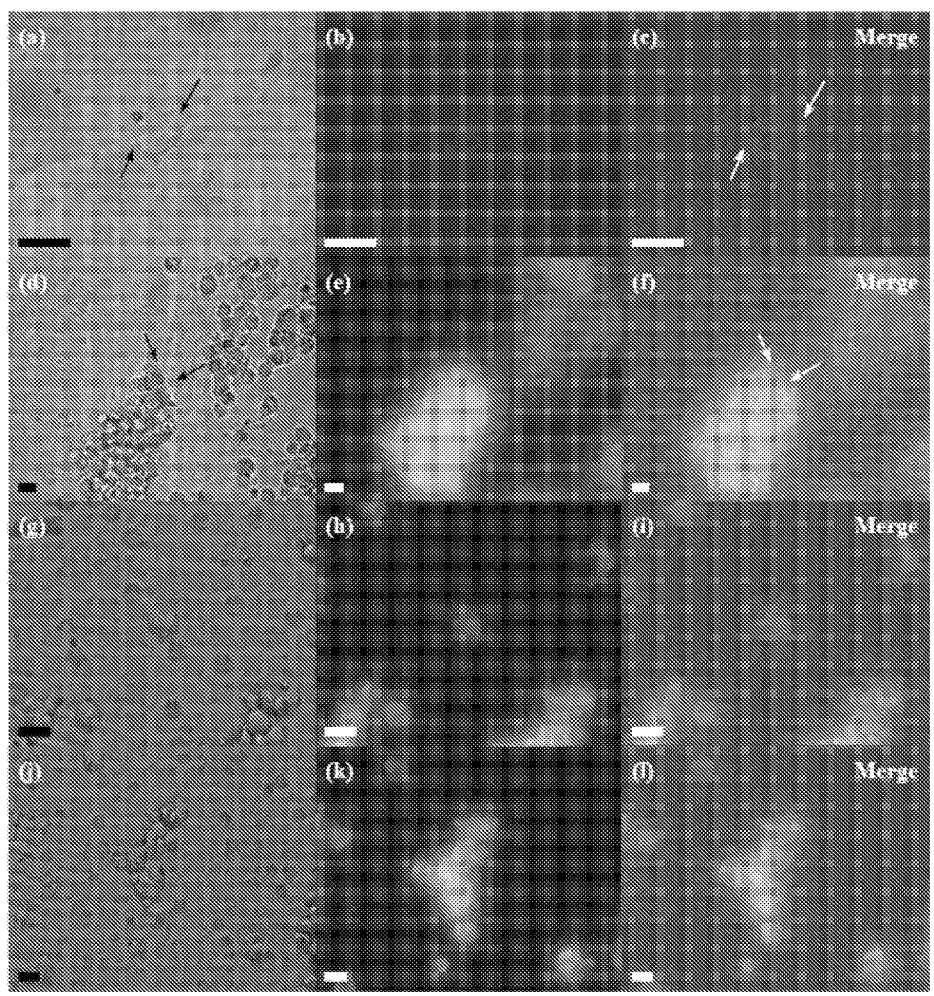
FIG. 13 shows fluorescent staining of F-Actin in cells which generate wrinkle patterns. (a) A fixed individual T24 cell generating a wrinkle pattern consisting of 2 wrinkles with an average length of 40 µm. (b) Fluorescently stained F-actin in the T24 cell from (a). (c) Merge of (a) & (b) where both images are 60% opaque. (d) A fixed cluster of T24 cells generating a wrinkle pattern consisting of 2 wrinkles with an average length of 60 µm. (e) Fluorescently stained F-actin in the T24 cell cluster from (d). (f) Merge of (d) & (e) where both images are 60% opaque. (g) A fixed individual HEK293f cell. (h) Fluorescently stained F-actin in the HEK293f cell from (g). (i) Merge of (g) & (h) where both images are 60% opaque. (j) A fixed cluster of HEK293f cells. (k) Fluorescently stained F-actin in the cluster of HEK293f cells from (j). (l) Merge of (j) & (k) where both images are 60% opaque. All cells were fixed after more than 12 hours. All scale bars are 20 µm.

Next, we validated that cancerous cells are mechanically capable of generating sufficient strain to induce deformation 24 hours of incubation of on the membrane, we fixed and stained T24 or HEK293f cells to visualize the localization of f-actin relative to wrinkle formation. Individual (FIG. 13(a)-(c)) and clusters (FIG. 13(d)-(f)) of T24 cells both generated two wrinkles, and more importantly the fluorescently stained f-actin co-localized with these wrinkles. Within an individual T24 cell, a locus of f-actin co-localized with the origins of wrinkles produced by the cell (FIG. 13(c)).

Figure 4:
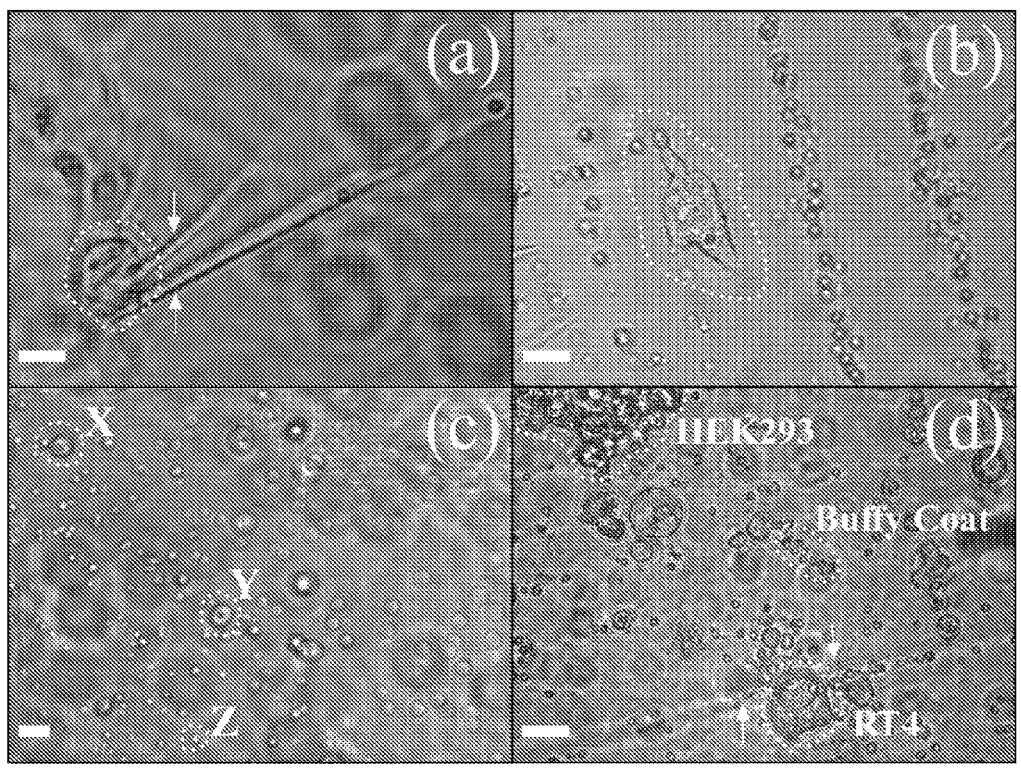
FIGS. 4(a)-4(d) are photographs taken of a representative membrane after incubation with various cell types. 4(a) Cancerous (RT4) cells, after 5 hours of incubation, form wrinkles at the outer edges of the RT4 cell cluster (dotted enclosure indicates the cluster and arrows indicate the wrinkle). 4(b) Non-cancerous (HEK293f) cells after 24 hrs of incubation: no membrane deformation was observed. 4(c) Buffy coat after 20 hours of incubation do not form wrinkles (X, Y, Z show a white blood cell, a red blood cell, and a platelet, respectively). 4(d) All cell types after 20 hours of incubation. Only the cancerous cells, circled by a dotted enclosure, wrinkle the membrane. Scale bar is 20 µm.
Figure 14:
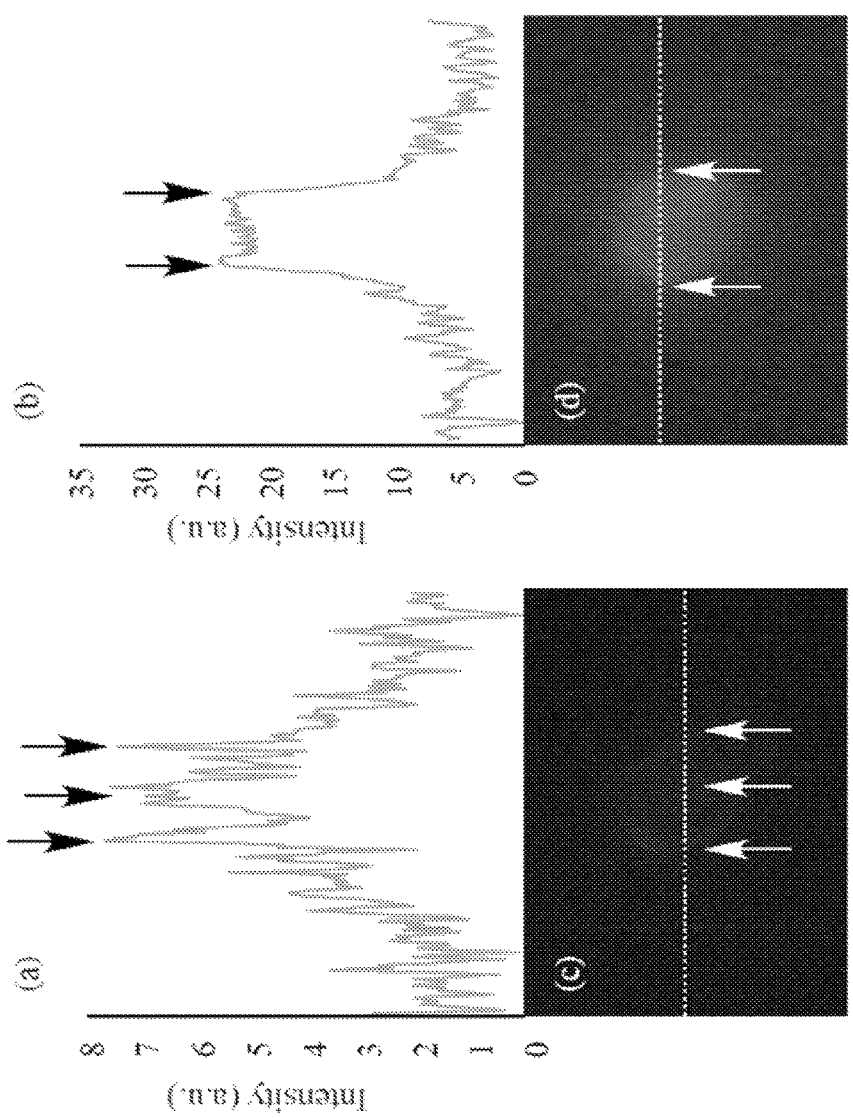
FIG. 14 shows fluorescent intensity traces comparing F-Actin in T24 & HEK293f cells. (a) and (b) are intensity traces which follow the dashed white lines in (c) and (d), respectively. (c) is a fluorescently stained T24 cell. (d) is a fluorescently stained HEK293f cell. Arrows indicate spikes in the intensity traces and the corresponding areas of the stained cells responsible for spikes.

An intensity trace of fluorescence adjacent to the wrinkle showed a dramatic increase in fluorescence, and thus and increased presence f-actin at this location (FIGS. 4(a) and (c)). In contrast, individual and clusters of HEK293f cells failed to generate wrinkles (FIGS. 13(g)-(l)), did not have any discernable locus of f-actin, and the fluorescent intensity trace showed homogeneous intensity within the cell (FIGS. 14(b) and (d)). The co-localization of an f-actin locus immediately adjacent to the origin of the wrinkle patterns generated by cancerous T24 cells, along with the lack an f-actin locus in non-cancerous HEK293f cells, which fail to induce wrinkling, supports the cytoskeleton of cancerous cells inducing the deformation of the membrane and ultimately for wrinkle pattern formation. This indicates that the cytoskeleton of the T24 cell is exerting a force on the ultra-thin membrane which does induce wrinkle pattern formation. Thus the underlying mechanism for membrane wrinkle formation appears dependent on f-actin foci and thus the cytoskeleton. While ancillary for clinical evaluation of patient samples, examining the underlying mechanism for wrinkle pattern formation gives insight into the inherent biophysical differences behind wrinkle pattern formation.

Conclusion.

Results from our double-blind study on human patients with bladder cancer-like symptoms show that cells extracted from clinical urine samples can selectively deform our ultra-thin silicone membrane and generate wrinkle patterns. In contrast, cells extracted from the urine of healthy donors fail to sufficiently induce wrinkle formation. We confirm via manipulation and labeling of cellular adhesion proteins that this innate difference in the ability to generate wrinkle patterns in our membrane is in part due to the unique biophysical properties of cancerous cells from healthy counter parts. Thus, our ultra-thin silicone membrane has the potential to be developed into a simple, yet cost effective tool to discern the presence of bladder cancer from cells present in urine samples.

Furthermore, our methodology can be applied toward the diagnosis of additional cancers where cells are easily obtained or naturally expelled, e.g. lung cancer detection through analysis of sputum. Moreover, our cancer diagnosis approach is highly amenable to developing nations where conventional diagnosis is cost-prohibitive and impedes continuous monitoring for initial onset and recurrences of cancer. Our device leverages inherent biophysical properties of cancerous cells for non-invasive, improved early detection and continuous surveillance for the recurrence of cancer.

Materials and Methods.

Device Fabrication.

As previously described, ultra-thin silicone membranes were formed by adding ~45 μL of 12,500 cP viscosity liquid silicone (Brookfield Engineering Laboratories) to a 15 mm by 0.5 mm glass depression slide (Ted Pella, Inc.). The uppermost layer of silicone was cross-linked by inverting the slide over a flame for 5 to 10 seconds. The cell culture chamber was formed by attaching a 1.9 cm diameter by 2.54 cm height section of sterile PVC with vacuum grease to the glass slide (FIG. 6(a)) [12]. In some experiments, ultra-thin silicone membrane surfaces were modified by the addition of 10 μg fibronectin (BD Biosciences) in 1×PBS, incubated at room temperature for 1 hour, aspirated and membranes washed three times with 1×PBS.

Cell Culture.

RT4 is an established bladder cell-line derived from low grade human transitional cell papilloma. T24 is derived from high grade human transitional cell carcinoma. HEK293f is a transformed human embryonic kidney cell-line that served as non-cancerous controls to simulate epithelial cells found in non-cancerous urine samples. RT4 and T24 cells were grown in McCoy's 5A modified media (Life Technologies) and HEK293f cells were grown in Eagle's minimum essential medium (ATCC). Media was supplemented with 10% fetal bovine serum (FBS, Life Technologies), and 1× penicillin/streptomycin (Sigma-Aldrich). Cells were maintained in a 5% $CO_2$ environment at 37° C.

Cell-Line Sample Preparation.

Cells at 80% confluency were trypsinized (Invitrogen) or incubated with cell dissociation buffer (Life Technologies) for 5 min at 37° C. and washed with media supplemented with 10% FBS. Approximately $5 \times 10^5$ cells were applied to each device and incubated in culture media with at 5% $CO_2$ at 37° C. For simulating clinical samples with hematuria, $5 \times 10^5$ white blood cells from buffy coat (Innovative Research) were applied to the ultra-thin membrane prior to applying RT4 or HEK293f. For urine pH effect, artificial urine (Spectrum Laboratories Inc.) or clarified aggregated donor urine samples were supplemented with 10% FBS and the pH adjusted with hydrochloric acid.

Patient and Healthy Donor Sample Preparation.

Five patient urine samples were obtained from men ages 53 to 89 undergoing trans-urethral resection of bladder tumor (TURBT) [13] at VA Palo Alto Health Care System and a sixth urine sample was collected from a healthy female donor control with no family history of bladder cancer and only a single grandparent with lung cancer likely linked to smoking, age 26. Informed consent was obtained from all patients. Cells present in the urine were pelleted by centrifugation at 300× gravity, washed twice with 1×PBS and re-suspended in McCoy's 5A modified media supplemented with 10% FBS prior to application to the ultra-thin silicone membrane.

Data Analysis.

The pattern generated when a cluster or individual cell deforms the ultra-thin membrane is defined as a wrinkle pattern. Wrinkle patterns consist of a number of wrinkles which have various lengths. In addition, wrinkle patterns were quantified by measuring the number and length of each wrinkle following addition of cells to ultra-thin silicone membrane.

Fluorescent Imaging.

F-actin was fluorescently labeled with Alexa Fluor 488 Phalloidin phallotoxin (Life Technologies) following the manufacturer's instructions. Briefly, T24 and HEK293f cells were pre-incubated on the ultra-thin silicone membrane for 24 hours were fixed with 4% paraformaldehyde in 1×PBS for 10 min at 37° C., washed twice with 1×PBS, permeabilized with 0.1% Triton X-100 in 1×PBS for 10 min at 37° C. and washed twice with 1×PBS. The permeabilized cells were incubated with fluorescent Alexa Fluor 488 Phalloidin phallotoxin for 20 min at room temperature, washed twice with 1×PBS and visualized under a confocal microscope (Nikon Eclipse TE2000-U). Fluorescent intensity traces were measured using Image J and the data was binned for every 4 values.

Supplementary Text.
Ultra-Thin Membrane Characterization Theory.

Figure 6:
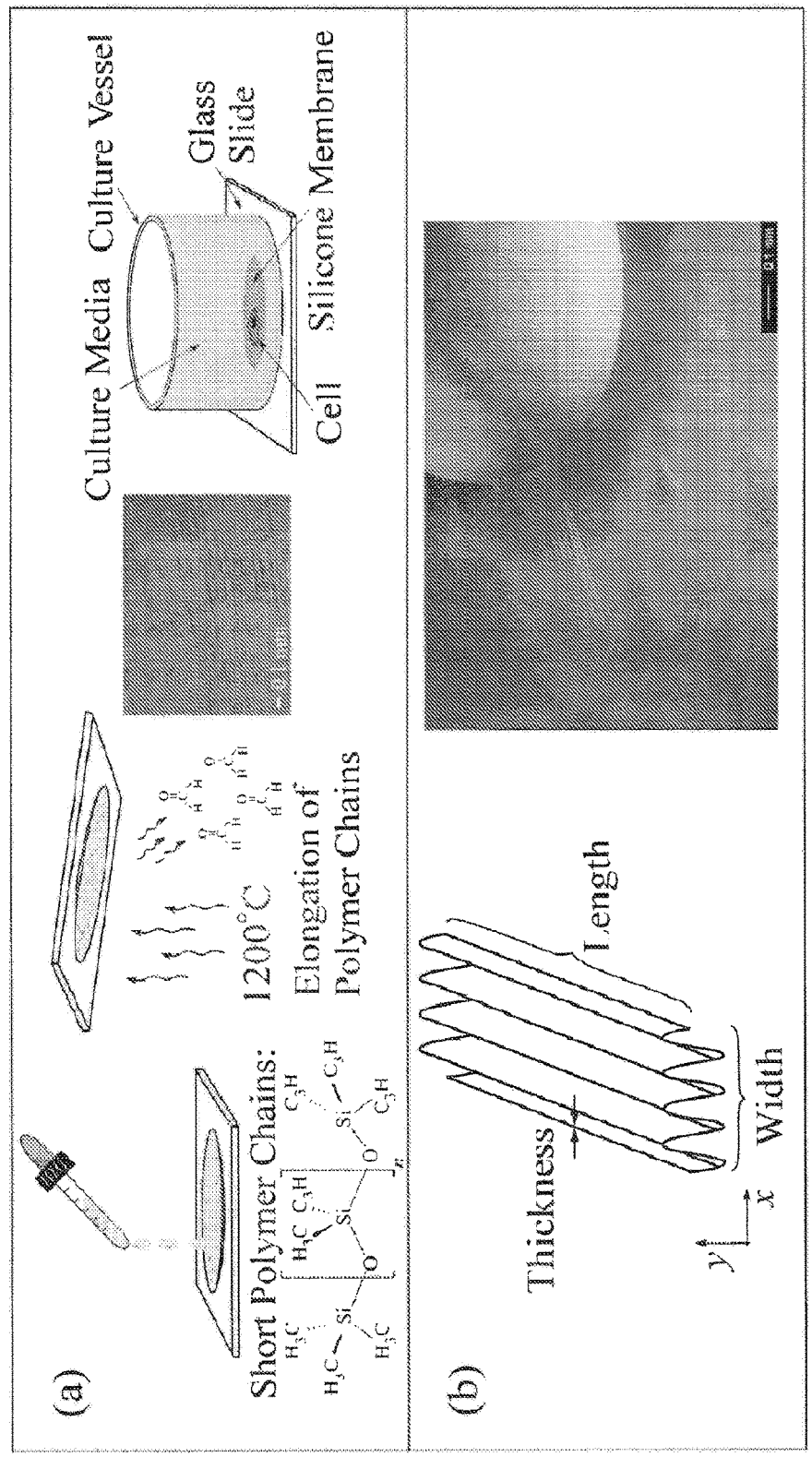
FIG. 6 shows membrane characterization and fabrication. (a) Membrane fabrication method, beginning with high viscosity liquid silicone in a concave glass slide, then the top layer of the liquid silicone is cross-linked via heat forming the ultra-thin membrane; a culture vessel is then applied creating a water-tight seal with the glass slide. (b) Membrane characterization method, using water droplets to determine membrane thickness.

To obtain predictive estimation of the wavelength, amplitude and number of wrinkles, we consider the 1D out-of-plane displacement of an initially flat sheet of area (W×L, where W is width and L is length) as a function of spatial dimension ($\xi(x,y)$) (FIG. 6($b$)). The thickness of the sheet, t, is much smaller than W and L, where 0<y<W, for simplicity, W<<L. When a stretching strain ε is applied in the x direction, then the total energy of the system is:

$$U = U_B + U_S - L \tag{1}$$

Here $U_B$ is the bending energy due to deformation in the y direction:

$$U_B = \tfrac{1}{2} \int B(\partial y^2 \xi)^2 dA \tag{2}$$

where B is the bending stiffness. $U_S$ is the stretching energy in presence of tension T(x):

$$U_S = \tfrac{1}{2} \int T(x)(dx\xi)^2 dA \tag{3}$$

As the sheet wrinkles in the y direction under the action of a small compressive stress, it satisfies the condition of inextensibility, $$\int_0^L \left[ \tfrac{1}{2}(\partial y^2 \xi)^2 - \frac{\Delta(x)}{w} \right] dy = 0$$

This constraint is found in the final term of equation 1, $$\mathcal{L} = \int_A b(x) \left[ (\partial y \xi)^2 - \frac{\Delta(x)}{W} \right] dA \tag{4}$$

where b(x) is the Lagrange multiplier and Δ(x) imposed the compressive transverse displacement.

Boundary Conditions:

$$\xi(0,y) = 0 \quad \xi(L,y) = 0$$

After applying boundary conditions we determine:

$$\lambda = \frac{\sqrt{2\pi L t}}{(3(1-v^2)\varepsilon)^{1/4}} \tag{5}$$

$$A = \sqrt{vLt} \left( \frac{16\varepsilon}{3\pi^2(1-v^2)} \right)^{1/4} \tag{6}$$

where λ is the wavelength and A is the amplitude of the sinusoidal wrinkling (FIG. 6 ($b$)), L is the length of the membrane, t is the thickness of the membrane, v is the Poisson's ratio of the membrane, and ε is the strain of the membrane [20]. We approximated the number of wrinkles by dividing the wavelength of the wrinkle pattern by the circumference of the water droplet (πd/λ), where d is the diameter of the droplet.

REFERENCES CITED (EXAMPLE 2)

[1] American Cancer Society. Cancer.org. 2015.
[2] S. Aldousari, and W. Kassouf, "Update on the management of non-muscle invasive bladder cancer" Can Urol Assoc J, 4(1): 56-64, February 2010.
[3] J. M. Tomasini and B. R. Konety, "Urinary Markers/Cytology What and When Should a Urologist Use" Urol Clin North Am. 40(2):165-73 May 2013.
[4] G. Cheung, A. Sahai, M. Billia, P. Dasgupta, and M. S. Khan, "Recent advances in the diagnosis and treatment of bladder cancer," BMC medicine, vol. 11, p. 13, 2013.
[5] M. Lekka, P. Laidler, D. Gil, J. Lekki, Z. Stachura, and a. Z. Hrynkiewicz, "Elasticity of normal and cancerous human bladder cells studied by scanning force microscopy," European biophysics journal: EBJ, vol. 28, pp. 312-6, 1999.
[6] T. W. Remmerbach, et al. Cancer Research 69.5 (2009): 1728-32.
[7] J. L. Tan, J. Tien, D. M. Pirone, D. S. Gray, K. Bhadriraju, and C. S. Chen, "Cells lying on a bed of microneedles: an approach to isolate mechanical force," Proceedings of the National Academy of Sciences of the United States of America, vol. 100, pp. 1484-9, 2003.
[8] A. Ilyas, W. Asghar, S. Ahmed, Y. Lotan, J.-T. Hsieh, Y.-t. Kim and S. M. Iqbal, "Electrophysiological analysis of biopsy samples using elasticity as an inherent cell marker for cancer detection" Analytical Methods, 2014.
[9] A. Harris, P. Wild, and D. Stopak, "Silicone Rubber Substrata: A New Wrinkle in the Study of Cell Locomotion" Science, vol. 208, pp. 177-179, 1980.
[10] R. J. Pelham and Y. L. Wang, "High resolution detection of mechanical forces exerted by locomoting fibroblasts on the substrate," Molecular biology of the cell, vol. 10, pp. 935-45, 1999.
[11] Z. Li, J. Song, G. Mantini, M.-Y. Lu, H. Fang, C. Falconi, L.-J. Chen, and Z. L. Wang, "Quantifying the Traction Force of a Single Cell by Aligned Silicon Nanowire Array" Nano Letters, vol. 9 issue 10 pp. 3575-3580, 2009.
[12] J. Appel, M. L. Y. Sin, J. C. Liao, J. Chae, "Wrinkle Cellomics: Screening Bladder Cancer Cells using an Ultra-Thin Silicone Membrane," Poster session presented at: IEEE 27th International Conference on Micro Electro Mechanical Systems (MEMS). 2014 Jan. 26-30. San Francisco, Calif.
[13] M. Babjuk, "Transurethral Resection of Non-muscle-invasive Bladder Cancer" European Urology Supplements, vol. 8, pp. 542-548, 2009.
[14] J. Huang, M. Juszkiewicz, W. H. de Jeu, E. Cerda, T. Emrick, N. Menon, et al., "Capillary wrinkling of floating thin polymer films," Science, vol. 317, pp. 650-3, 2007.
[15] E. Cerda and L. Mahadevan, "Geometry and Physics of Wrinkling", Physical Review Letters, 90, 2003.
[16] M. E. Wright, D. S. Michaud, P Pietinen, P. R. Taylor, J. Virtamo, D. Albanes, "Estimated urine pH and bladder cancer risk in a cohort of male smokers (Finland)." Cancer Causes and Control, vol. 16, issue 9, pp. 1117-23, November 2005.
[17] M. Casey, Kraning-Rush, J. P. Califano, C. A. Reinhart-King, "Cellular Traction Stresses Increase with Increasing Metastatic Potential" PLoS ONE 7(2): e32572.
[18] T. M Koch, S. Münster, N. Bonakdar, J. P. Butler, B. Fabry (2012) "3D Traction Forces in Cancer Cell Invasion". PLoS ONE 7(3): e33476.
[19] D.-H. Kim, S. B. Khatau, Y. Feng, S. Walcott, S. X. Sun, G. D. Longmore, D. Wirtz, "Actin cap associated focal adhesions and their distinct role in cellular mechanosensing" Scientific Reports, vol. 2, article 555, 2012.
[20] E. Cerda and L. Mahadevan, "Geometry and Physics of Wrinkling", Physical Review Letters, 90, 2003.

The invention claimed is:

1. A method for detecting the presence of one or more cancer cells in a biological sample, the method comprising:
   contacting a thin film comprising a cross-linked polysiloxane with at least a portion of a biological sample and a culture media; and
   detecting the presence or absence of one or more wrinkles in the thin film, whereby the presence of one or more wrinkles indicates that the biological sample contains one or more cancer cells.

2. The method of claim 1, wherein the cross-linked polysiloxane is a cross-linked polydimethylsiloxane.

3. The method claim 2, wherein the cross-linked polydimethylsiloxane is a cross-linked liquid silicone.

4. The method of 1, wherein the polysiloxane is cross-linked by heating the polysiloxane.

5. The method of claim 1, wherein the thin film is between 5 nm and 1,000 nm thick.

6. The method of claim 5, wherein the thin film is between 5 nm and 500 nm thick.

7. The method of claim 6, wherein the thin film is between 5 nm and 100 nm thick.

8. The method of claim 7, wherein the thin film is between 10 nm and 50 nm thick.

9. The method of claim 1, wherein the step of detecting the presence or absence of one or more wrinkles in the thin film is performed by visually inspecting the thin film.

10. The method of claim 9, wherein the step of visually inspecting the thin film is performed using conventional light microscopy.

11. The method of claim 1, wherein the cancer cells are bladder cancer cells.

12. The method of claim 1, wherein the biological sample comprises a fluid selected from the group consisting of urine, blood, saliva, lymph, and cerebrospinal fluid.

13. A method of screening for cancer in a subject, the method comprising:
   contacting a thin film comprising a cross-linked polysiloxane with a culture media and at least a portion of a biological sample obtained from the subject; and
   detecting the wrinkle pattern of the thin film, whereby the nature of the wrinkle pattern indicates the potential presence of cancer in the subject.

14. The method of claim 13, wherein the polysiloxane is cross-linked by heating the polysiloxane.

15. The method of claim 13, wherein the wrinkle pattern is detected by visualizing the thin film.

16. The method of claim 15, wherein the thin film is visualized using conventional light microscopy.

17. The method of claim 13, wherein the wrinkle pattern is quantitatively measured.

18. The method of claim 17, wherein a higher quantity of wrinkles in the wrinkle pattern indicates a higher likelihood of the subject having cancer.

19. The method of claim 17, wherein a longer length of wrinkles in the wrinkle pattern indicates a higher likelihood of the subject having cancer.

20. The method of claim 13, wherein the cross-linked polysiloxane is a cross-linked polydimethylsiloxane.

21. The method claim 20, wherein the cross-linked polydimethylsiloxane is a cross-linked liquid silicone.

22. The method of claim 13, wherein the thin film is between 5 nm and 1,000 nm thick.

23. The method of claim 22, wherein the thin film is between 5 nm and 500 nm thick.

24. The method of claim 23, wherein the thin film is between 5 nm and 100 nm thick.

25. The method of claim 24, wherein the thin film is between 10 nm and 50 nm thick.

26. The method of claim 13, wherein the type of cancer that is screened for is bladder cancer.

27. The method of claim 13, wherein the biological sample comprises a fluid selected from the group consisting of urine, blood, saliva, lymph, and cerebrospinal fluid.

28. A kit for performing a cancer screening assay, the kit comprising:
   a thin film having a thickness of from 5 nm to 500 nm comprising a cross-linked polysiloxane; and
   a media for culturing cells.

29. The method of claim 28, wherein the cross-linked polysiloxane is a cross-linked polydimethylsiloxane.

30. The method claim 29, wherein the cross-linked polydimethylsiloxane is a cross-linked liquid silicone.

31. The method of claim 28, wherein the thin film is between 5 nm and 100 nm thick.

32. The method of claim 31, wherein the thin film is between 10 nm and 50 nm thick.

* * * * *